(12) United States Patent
Morris et al.

(10) Patent No.: US 10,512,264 B2
(45) Date of Patent: Dec. 24, 2019

(54) HERBICIDAL MIXTURES

(71) Applicant: Syngenta Participations AG, Basel (CH)

(72) Inventors: James Alan Morris, Bracknell (GB); Jutta Elisabeth Boehmer, Bracknell (GB); William Guy Whittingham, Bracknell (GB); Timothy Robert Desson, Bracknell (GB); Anne Jacqueline Dalencon, Bracknell (GB); Brian Pickett, Bracknell (GB); Nikolaos Kaloumenos, Bracknell (GB); Akos Balogh, Basel (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/562,652

(22) PCT Filed: Mar. 24, 2016

(86) PCT No.: PCT/EP2016/056631
§ 371 (c)(1),
(2) Date: Sep. 28, 2017

(87) PCT Pub. No.: WO2016/156241
PCT Pub. Date: Oct. 6, 2016

(65) Prior Publication Data
US 2018/0084778 A1 Mar. 29, 2018

(30) Foreign Application Priority Data
Apr. 2, 2015 (GB) .................................. 1505740.9

(51) Int. Cl.
| | |
|---|---|
| *A01N 37/22* | (2006.01) |
| *A01N 41/10* | (2006.01) |
| *A01N 43/40* | (2006.01) |
| *A01N 43/54* | (2006.01) |
| *A01N 43/80* | (2006.01) |
| *A01N 43/36* | (2006.01) |
| *A01N 43/56* | (2006.01) |
| *A01N 43/70* | (2006.01) |

(52) U.S. Cl.
CPC ............ *A01N 43/36* (2013.01); *A01N 37/22* (2013.01); *A01N 41/10* (2013.01); *A01N 43/40* (2013.01); *A01N 43/54* (2013.01); *A01N 43/56* (2013.01); *A01N 43/70* (2013.01); *A01N 43/80* (2013.01); *A01N 2300/00* (2013.01)

(58) Field of Classification Search
CPC combination set(s) only.
See application file for complete search history.

(56) References Cited

U.S. PATENT DOCUMENTS 9,936,701 B2 * 4/2018 Morris .................. A01N 43/80

FOREIGN PATENT DOCUMENTS

| WO | 2014180740 A1 | 11/2014 |
| WO | 2015018431 A1 | 2/2015 |
| WO | 2015018434 A1 | 2/2015 |

OTHER PUBLICATIONS

Notification of Transmittal of the International Search Report for International Application No. PCT/EP2016/056631 dated May 23, 2017.

* cited by examiner

*Primary Examiner* — John Pak
(74) *Attorney, Agent, or Firm* — BakerHostetler LLP; Toni-Junell Herbert

(57) ABSTRACT

The present invention provides a composition comprising (A) a compound of formula (I) wherein $R^1$ is methyl, methoxy or chloro, $R^2$ is methyl or chloro and A is a substituted heteroaryl group, or an N-oxide or salt form thereof, and (B) one or more further herbicides; as well as the use of such compositions in controlling plants or inhibiting plant growth.

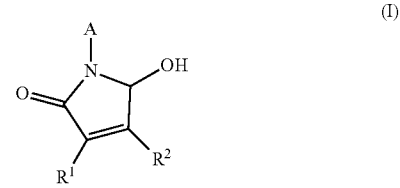

(I)

13 Claims, No Drawings

HERBICIDAL MIXTURES

RELATED APPLICATION INFORMATION

This application is a 371 of International Application No. PCT/EP2016/056631, filed Mar. 24, 2016, which claims priority to GB Application No. 1505740.9 filed Apr. 2, 2015, the contents of which are incorporated herein by reference herein.

The present invention relates novel herbicidal compositions and their use in controlling plants or inhibiting plant growth.

Herbicidal pyrrolones of the formula

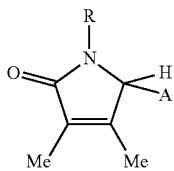

wherein A is hydroxy, halogen or OAcyl; and R is an optionally substituted aryl, aralkyl or heteroaryl group are taught in Swiss patent application CH633678.

Further herbicidal pyrrolones of the formula

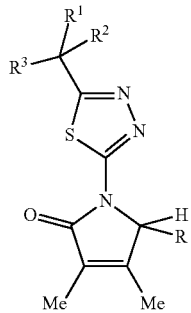

wherein R is, inter alia, OH, $R^1$ is H or alkyl, and $R^2$ and $R^3$ are alkyl, haloalkyl, or alkylene are taught in EP0286816A1.

Further herbicidal pyrrolones of the formula

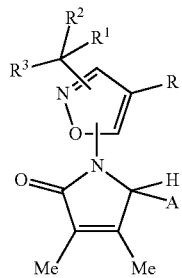

wherein A is e.g. OH, R is H, halogen, alkyl, haloalkyl, or alkoxyl, $R^1$ to $R^3$ are each H, halogen, alkyl, haloalkyl, alkyoxyalkyl, or $R^2$ and $R^3$ together form a 3 to 7 membered ring; are disclosed in EP0297378A2.

Further herbicidal pyrrolones of the formula

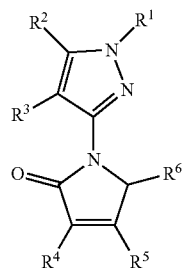

wherein $R^1$ is H, alkyl, haloalkyl, alkenyl, haloalkenyl, alkynyl, alkoxyalkyl or optionally substituted aryl or aralkyl, $R^2$ is H, alkyl, haloalkyl, alkenyl, haloalkenyl, alkynyl, alkoxyalkyl, alkylthioalkyl or optionally substituted cycloalkyl or aryl, $R^3$, $R^4$ and $R^5$ are, inter alia, H or alkyl and $R^6$ is, inter alia, OH are disclosed in EP0334133.

The object of the present invention is to provide herbicidal mixtures which are highly effective against various weed species at low does and/or have increased crop tolerance.

SUMMARY OF THE INVENTION

In one aspect, therefore, the present invention therefore provides a composition comprising (A) a compound of formula (I):

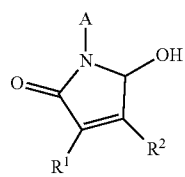

wherein $R^1$ is methyl, methoxy or chloro, $R^2$ is methyl or chloro and A is a substituted heteroaryl group and wherein said compound is selected from the group consisting of 1.1

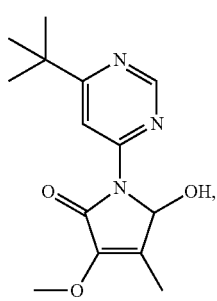

1.2

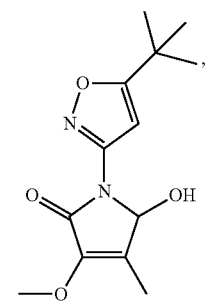

-continued

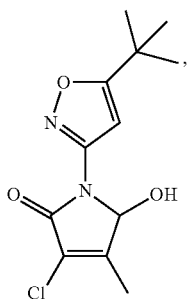

1.3

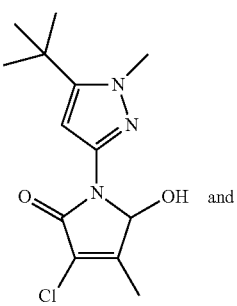

1.4 and

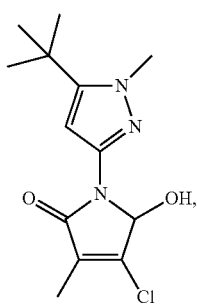

1.5 or an N-oxide or salt form thereof,
and (B) one or more herbicides selected from the group comprising acetochlor, acifluorfen-sodium, aclonifen, alachlor, alloxydim, ametryn, amicarbazone, amidosulfuron, aminocyclopyrachlor, aminopyralid, amitrole, asulam, atrazine, beflubutamid, benfluralin, bensulfuron-methyl, bentazone, bicyclopyrone, bifenox, bispyribac-sodium, bromacil, bromoxynil, butafenacil, cafenstrole, carfentrazone-ethyl, chloransulam, chlorimuron-ethyl, chlorotoluron, chlorsulfuron, cinosulfuron, cinidon-ethyl, clethodim, clodinafop-propargyl, clomazone, clopyralid, cycloxydim, cyhalofop-butyl, 2,4-D (including the choline salt and 2-ethylhexyl ester thereof), daimuron, desmedipham, dicamba (including the aluminum, aminopropyl, bis-aminopropylmethyl, choline, diglycolamine, dimethylamine, dimethylammonium, potassium and sodium salts thereof), diclofop-methyl, diclosulam, difenzoquat, diflufenican, diflufenzopyr, dimethachlor, dimethenamid-P, diquat dibromide, diuron, esprocarb, ethametsulfuron, ethofumesate, fenoxaprop-P-ethyl, fenquinotrione, flazasulfuron, florasulam, fluazifop-P-butyl, flucarbazone-sodium, flufenacet, flumetralin, flumetsulam, flumioxazin, flupyrsulfuron-methyl-sodium, fluroxypyr-meptyl, flurtamone, fluthiacet-methyl, fomesafen, foramsulfuron, glufosinate (including the ammonium salt thereof), glyphosate (including the diammonium, isopropylammonium and potassium salts thereof), halauxifen-methyl, halosulfuron-methyl, haloxyfop-methyl, hexazinone, imazamethabenz, imazamox, imazapic, imazapyr, imazaquin, imazethapyr, indaziflam, iodosulfuron-methyl-sodium, iofensulfuron, iofensulfuron-sodium, ioxynil, ipfencarbazone, isoproturon, isoxaben, isoxaflutole, lactofen, linuron, MCPA, MCPP, mecoprop-P, mefenacet, mesosulfuron, mesosulfuron-methyl, mesotrione, metamitron, metazachlor, metobromuron, metolachlor, metoxuron, metribuzin, metsulfuron, molinate, napropamide, nicosulfuron, norflurazon, orthosulfamuron, oxadiargyl, oxadiazon, oxasulfuron, oxyfluorfen, paraquat dichloride, pendimethalin, penoxsulam, pethoxamid, phenmedipham, picloram, picolinafen, pinoxaden, pretilachlor, primisulfuron-methyl, prodiamine, prometryn, propachlor, propanil, propaquizafop, propham, propoxycarbazone, propyzamide, prosulfocarb, prosulfuron, pyrasulfotole, pyrazolynate, pyrazosulfuron-ethyl, pyribenzoxim, pyridate, pyriftalid, pyrithiobac-sodium, pyroxasulfone, pyroxsulam, quinclorac, quizalofop-P-ethyl, rimsulfuron, saflufenacil, sethoxydim, S-metolachlor, sulcotrione, sulfentrazone, sulfometuron-methyl, sulfosulfuron, tebuthiuron, tefuryltrione, tembotrione, terbuthylazine, terbutryn, thiencarbazone, thifensulfuron, tiafenacil, tolpyralate, topramezone, tralkoxydim, triafamone, triallate, triasulfuron, tribenuron-methyl, triclopyr, trifloxysulfuron-sodium, trifludimoxazin, trifluralin, tritosulfuron and 4-amino-3-chloro-6-(4-chloro-2-fluoro-3-methoxyphenyl)-5-fluoro-pyridine-2-carboxylate.

In a second aspect, the invention provides the use of a composition of the invention as a herbicide.

In a third aspect, the invention provides a method of controlling plants, comprising applying to the plants or to the locus of the plants, a herbicidally effective amount of a composition of the invention.

In a fourth aspect, the invention provides a method of inhibiting plant growth, comprising applying to the plants or to the locus thereof, a herbicidally effective amount of a composition of the invention.

In a fifth aspect, the invention provides a method of controlling weeds in crops of useful plants, comprising applying to the weeds or to the locus of the weeds, or to the useful plants or to the locus of the useful plants, a herbicidally effective amount of a composition of the invention.

In a sixth aspect, the invention provides a method of selectively controlling grasses and/or weeds in crops of useful plants which comprises applying to the useful plants or locus thereof or to the area of cultivation a herbicidally effective amount of a composition of the invention.

DETAILED DESCRIPTION

Particularly preferred embodiments of the invention are as set out below.

Preferably, (B) is a herbicide selected from the group consisting of acetochlor, acifluorfen-sodium, alachlor, amidosulfuron, aminopyralid, atrazine, beflubutamid, benfluralin, bensulfuron-methyl, bicyclopyrone, bifenox, bispyribac-sodium, bromoxynil, butafenacil, carfentrazone-ethyl, chloransulam, chlorimuron-ethyl, chlorotoluron, chlorsulfuron, cinosulfuron, cinidon-ethyl, clethodim, clodinafop-propargyl, clopyralid, cycloxydim, 2,4-D (including the choline salt and 2-ethylhexyl ester thereof), dicamba (including the aluminum, aminopropyl, bis-aminopropylmethyl, choline, diglycolamine, dimethylamine, dimethylammonium, potassium and sodium salts thereof), diclofop-methyl, diclosulam, diflufenican, dimethachlor, dimethenamid-P, diquat dibromide, ethametsulfuron, fenoxaprop-P-ethyl, flazasulfuron, florasulam, fluazifop-P-butyl, flucarbazone-sodium, flufenacet, flumetsulam, flumioxazin, flupyrsulfuron-methyl-sodium, fluroxypyr-meptyl, flurtamone, fluthiacet-methyl, fomesafen, foramsulfuron, glufosinate (including the ammonium salt thereof), glyphosate (including the diammonium, isopropylammonium and potassium salts thereof), halauxifen-methyl, haloxyfop-methyl, hexazinone, imazamethabenz, imazamox, imazapic, imazapyr, imazethapyr, iodosulfuron-methyl-sodium, iofensulfuron, iofensulfuron-sodium, isoproturon, isoxaben, isoxaflutole, lactofen, MCPA, MCPP, mesosulfuron, mesosulfuron-methyl, mesotrione, metazachlor, metobromuron, metribuzin, metsulfuron, napropamide, nicosulfuron, oxadiazon, oxasulfuron, oxyfluorfen, paraquat dichloride, pendimethalin, penoxsulam, pethoxamid, picolinafen, pinoxaden, pretilachlor, primisulfuron-methyl, propoxycarbazone, prosulfocarb, prosulfuron, pyrasulfotole, pyribenzoxim, pyriftalid, pyrithiobac-sodium, pyroxasulfone, pyroxsulam, quizalofop-P-ethyl, rimsulfuron, saflufenacil, sethoxydim, S-metolachlor, sulcotrione, sulfentrazone, sulfometuron-methyl, sulfosulfuron, tembotrione, terbuthylazine, thiencarbazone, thifensulfuron, topramezone, triallate, triasulfuron, tribenuron-methyl, trifloxysulfuron-sodium, trifluralin, tritosulfuron and 4-amino-3-chloro-6-(4-chloro-2-fluoro-3-methoxyphenyl)-5-fluoropyridine-2-carboxylate.

More preferably, (B) is a herbicide selected from the group consisting of acetochlor, alachlor, amidosulfuron, aminopyralid, atrazine, beflubutamid, benfluralin, bicyclopyrone, bifenox, bromoxynil, butafenacil, carfentrazone-ethyl, chlorotoluron, clodinafop-propargyl, clopyralid, 2,4-D (including the choline salt and 2-ethylhexyl ester thereof), dicamba (including the aluminum, aminopropyl, bis-aminopropylmethyl, choline, diglycolamine, dimethylamine, dimethylammonium, potassium and sodium salts thereof), diclofop-methyl, diflufenican, dimethachlor, dimethenamid-P, diquat dibromide, fenoxaprop-P-ethyl, florasulam, fluazifop-P-butyl, flucarbazone-sodium, flufenacet, flumetsulam, flumioxazin, flupyrsulfuron-methyl-sodium, fluroxypyr-meptyl, flurtamone, fluthiacet-methyl, glufosinate (including the ammonium salt thereof), glyphosate (including the diammonium, isopropylammonium and potassium salts thereof), halauxifen-methyl, hexazinone, iodosulfuron-methyl-sodium, isoproturon, isoxaben, isoxaflutole, MCPA, MCPP, mesosulfuron, mesosulfuron-methyl, mesotrione, metobromuron, metribuzin, metsulfuron, nicosulfuron, paraquat dichloride, pendimethalin, pethoxamid, picolinafen, pinoxaden, propoxycarbazone, prosulfocarb, pyroxasulfone, pyroxsulam, saflufenacil, S-metolachlor, sulfosulfuron, tembotrione, terbuthylazine, thiencarbazone, topramezone, triallate, triasulfuron, tribenuron-methyl, trifloxysulfuron-sodium, trifluralin and 4-amino-3-chloro-6-(4-chloro-2-fluoro-3-m ethoxyphenyl)-5-fluoropyridine-2-carboxylate.

Even more preferably, (B) is a herbicide selected from the group consisting of acetochlor, alachlor, atrazine, benfluralin, bicyclopyrone, clopyralid, 2,4-D (including the choline salt and 2-ethylhexyl ester thereof), dicamba (including the aluminum, aminopropyl, bis-aminopropylmethyl, choline, diglycolamine, dimethylamine, dimethylammonium, potassium and sodium salts thereof), diflufenican, dimethachlor, dimethenamid-P, diquat dibromide, fluazifop-P-butyl, flufenacet, glufosinate (including the ammonium salt thereof), glyphosate (including the diammonium, isopropylammonium and potassium salts thereof), hexazinone, isoxaflutole, mesotrione, metribuzin, nicosulfuron, paraquat dichloride, pendimethalin, pinoxaden, prosulfocarb, pyroxasulfone, S-metolachlor, tembotrione, terbuthylazine, thiencarbazone, topramezone, triasulfuron and trifluralin.

Even more preferably, (B) is a herbicide selected from the group consisting of atrazine, bicyclopyrone, dimethachlor, flufenacet, glyphosate (including the diammonium, isopropylammonium and potassium salts thereof), isoxaflutole, mesotrione, nicosulfuron, S-metolachlor and terbuthylazine.

Most preferably (B) is a herbicide selected from the group consisting of atrazine, bicyclopyrone, mesotrione, S-metolachlor and terbuthylazine.

In one embodiment, (B) is atrazine.
In one embodiment (B) is bicyclopyrone.
In one embodiment (B) is mesotrione.
In one embodiment (B) is S-metolachlor.
In one embodiment (B) is terbuthylazine.
In one embodiment, (A) is compound 1.1.
In one embodiment (A) is compound 1.2.
In one embodiment (A) is compound 1.3.
In one embodiment (A) is compound 1.4.
In one embodiment (A) is compound 1.5.

Further example compositions of the invention comprise: compound 1.1+acetochlor, compound 1.1+acifluorfen-sodium, compound 1.1+aclonifen, compound 1.1+alachlor, compound 1.1+alloxydim, compound 1.1+ametryn, compound 1.1+amicarbazone, compound 1.1+amidosulfuron, compound 1.1+aminocyclopyrachlor, compound 1.1+aminopyralid, compound 1.1+amitrole, compound 1.1+asulam, compound 1.1+atrazine, compound 1.1+beflubutamid, compound 1.1+benfluralin, compound 1.1+bensulfuron-methyl, compound 1.1+bentazone, compound 1.1+bicyclopyrone, compound 1.1+bifenox, compound 1.1+bispyribac-sodium, compound 1.1+bromacil, compound 1.1+bromoxynil, compound 1.1+butafenacil, compound 1.1+cafenstrole, compound 1.1+carfentrazone-ethyl, compound 1.1+chloransulam, compound 1.1+chlorimuron-ethyl, compound 1.1+chlorotoluron, compound 1.1+chlorsulfuron, compound 1.1+cinosulfuron, compound 1.1+cinidon-ethyl, compound 1.1+clethodim, compound 1.1+clodinafop-propargyl, compound 1.1+clomazone, compound 1.1+clopyralid, compound 1.1+cycloxydim, compound 1.1+cyhalofop-butyl, compound 1.1+2,4-D (including the choline salt and 2-ethylhexyl ester thereof), compound 1.1+daimuron, compound 1.1+desmedipham, compound 1.1+dicamba (including the aluminum, aminopropyl, bis-aminopropylmethyl, choline, diglycolamine, dimethylamine, dimethylammonium, potassium and sodium salts thereof), compound 1.1+diclofop-methyl, compound 1.1+diclosulam, compound 1.1+difenzoquat, compound 1.1+diflufenican, compound 1.1+diflufenzopyr, compound 1.1+dimethachlor, compound 1.1+dimethenamid-P, compound 1.1+diquat dibromide, compound 1.1+diuron, compound 1.1+esprocarb, compound 1.1+ethametsulfuron, compound 1.1+ethofumesate, compound 1.1+fenoxaprop-P-ethyl, compound 1.1+fenquinotrione, compound 1.1+flazasulfuron, compound 1.1+florasulam, compound 1.1+fluazifop-P-butyl, compound 1.1+flucarbazone-sodium, compound 1.1+flufenacet, compound 1.1+flumetralin, compound 1.1+flumetsulam, compound 1.1+flumioxazin, compound 1.1+flupyrsulfuron-methyl-sodium, compound 1.1+fluroxypyr-meptyl, compound 1.1+flurtamone, compound 1.1+fluthiacet-methyl, compound 1.1+fomesafen, compound 1.1+foramsulfuron, compound 1.1+glufosinate (including the ammonium salt thereof), compound 1.1+glyphosate (including the diammonium, isopropylammonium and potassium salts thereof), compound 1.1+halauxifen-methyl, compound 1.1+halosulfuron-methyl, compound 1.1+haloxyfop-methyl, compound 1.1+hexazinone, compound 1.1+imazamethabenz, compound 1.1+imazamox, compound 1.1+imazapic, compound 1.1+imazapyr, compound 1.1+imazaquin, compound 1.1+imazethapyr, compound 1.1+indaziflam, compound 1.1+iodosulfuron-methyl-sodium, compound 1.1+ iofensulfuron, compound 1.1+iofensulfuron-sodium, compound 1.1+ioxynil, compound 1.1+ipfencarbazone, compound 1.1+isoproturon, compound 1.1+isoxaben, compound 1.1+isoxaflutole, compound 1.1+lactofen, compound 1.1+linuron, compound 1.1+MCPA, compound 1.1+MCPP, compound 1.1+mecoprop-P, compound 1.1+mefenacet, compound 1.1+mesosulfuron, compound 1.1+mesosulfuron-methyl, compound 1.1+mesotrione, compound 1.1+metamitron, compound 1.1+metazachlor, compound 1.1+metobromuron, compound 1.1+metolachlor, compound 1.1+metoxuron, compound 1.1+metribuzin, compound 1.1+metsulfuron, compound 1.1+molinate, compound 1.1+napropamide, compound 1.1+nicosulfuron, compound 1.1+norflurazon, compound 1.1+orthosulfamuron, compound 1.1+oxadiargyl, compound 1.1+oxadiazon, compound 1.1+oxasulfuron, compound 1.1+oxyfluorfen, compound 1.1+paraquat dichloride, compound 1.1+pendimethalin, compound 1.1+penoxsulam, compound 1.1+pethoxamid, compound 1.1+phenmedipham, compound 1.1+picloram, compound 1.1+picolinafen, compound 1.1+pinoxaden, compound 1.1+pretilachlor, compound 1.1+primisulfuron-methyl, compound 1.1+prodiamine, compound 1.1+prometryn, compound 1.1+propachlor, compound 1.1+propanil, compound 1.1+propaquizafop, compound 1.1+propham, compound 1.1+propoxycarbazone, compound 1.1+propyzamide, compound 1.1+prosulfocarb, compound 1.1+prosulfuron, compound 1.1+pyrasulfotole, compound 1.1+pyrazolynate, compound 1.1+pyrazosulfuron-ethyl, compound 1.1+pyribenzoxim, compound 1.1+pyridate, compound 1.1+pyriftalid, compound 1.1+pyrithiobac-sodium, compound 1.1+pyroxasulfone, compound 1.1+pyroxsulam, compound 1.1+quinclorac, compound 1.1+quizalofop-P-ethyl, compound 1.1+rimsulfuron, compound 1.1+saflufenacil, compound 1.1+sethoxydim, compound 1.1+S-metolachlor, compound 1.1+sulcotrione, compound 1.1+sulfentrazone, compound 1.1+sulfometuron-methyl, compound 1.1+sulfosulfuron, compound 1.1+tebuthiuron, compound 1.1+tefuryltrione, compound 1.1+tembotrione, compound 1.1+terbuthylazine, compound 1.1+terbutryn, compound 1.1+thiencarbazone, compound 1.1+thifensulfuron, compound 1.1+tiafenacil, compound 1.1+tolpyralate, compound 1.1+topramezone, compound 1.1+tralkoxydim, compound 1.1+triafamone, compound 1.1+triallate, compound 1.1+triasulfuron, compound 1.1+tribenuron-methyl, compound 1.1+triclopyr, compound 1.1+trifloxysulfuron-sodium, compound 1.1+trifludimoxazin, compound 1.1+trifluralin, compound 1.1+tritosulfuron and compound 1.1+4-amino-3-chloro-6-(4-chloro-2-fluoro-3-methoxyphenyl)-5-fluoro-pyridine-2-carboxylate;

compound 1.2+acetochlor, compound 1.2+acifluorfen-sodium, compound 1.2+aclonifen, compound 1.2+alachlor, compound 1.2+alloxydim, compound 1.2+ametryn, compound 1.2+amicarbazone, compound 1.2+amidosulfuron, compound 1.2+aminocyclopyrachlor, compound 1.2+aminopyralid, compound 1.2+amitrole, compound 1.2+asulam, compound 1.2+atrazine, compound 1.2+beflubutamid, compound 1.2+benfluralin, compound 1.2+bensulfuron-methyl, compound 1.2+bentazone, compound 1.2+bicyclopyrone, compound 1.2+bifenox, compound 1.2+bispyribac-sodium, compound 1.2+bromacil, compound 1.2+bromoxynil, compound 1.2+butafenacil, compound 1.2+cafenstrole, compound 1.2+carfentrazone-ethyl, compound 1.2+chloransulam, compound 1.2+chlorimuron-ethyl, compound 1.2+chlorotoluron, compound 1.2+chlorsulfuron, compound 1.2+cinosulfuron, compound 1.2+cinidon-ethyl, compound 1.2+clethodim, compound 1.2+clodinafop-propargyl, compound 1.2+clomazone, compound 1.2+clopyralid, compound 1.2+cycloxydim, compound 1.2+cyhalofop-butyl, compound 1.2+2,4-D (including the choline salt and 2-ethylhexyl ester thereof), compound 1.2+daimuron, compound 1.2+desmedipham, compound 1.2+dicamba (including the aluminum, aminopropyl, bis-aminopropylmethyl, choline, diglycolamine, dimethylamine, dimethylammonium, potassium and sodium salts thereof), compound 1.2+diclofop-methyl, compound 1.2+diclosulam, compound 1.2+difenzoquat, compound 1.2+diflufenican, compound 1.2+diflufenzopyr, compound 1.2+dimethachlor, compound 1.2+dimethenamid-P, compound 1.2+diquat dibromide, compound 1.2+diuron, compound 1.2+esprocarb, compound 1.2+ethametsulfuron, compound 1.2+ethofumesate, compound 1.2+fenoxaprop-P-ethyl, compound 1.2+fenquinotrione, compound 1.2+flazasulfuron, compound 1.2+florasulam, compound 1.2+fluazifop-P-butyl, compound 1.2+flucarbazone-sodium, compound 1.2+flufenacet, compound 1.2+flumetralin, compound 1.2+flumetsulam, compound 1.2+flumioxazin, compound 1.2+flupyrsulfuron-methyl-sodium, compound 1.2+fluroxypyr-meptyl, compound 1.2+flurtamone, compound 1.2+fluthiacet-methyl, compound 1.2+fomesafen, compound 1.2+foramsulfuron, compound 1.2+glufosinate (including the ammonium salt thereof), compound 1.2+glyphosate (including the diammonium, isopropylammonium and potassium salts thereof), compound 1.2+halauxifen-methyl, compound 1.2+halosulfuron-methyl, compound 1.2+haloxyfop-methyl, compound 1.2+hexazinone, compound 1.2+imazamethabenz, compound 1.2+imazamox, compound 1.2+imazapic, compound 1.2+imazapyr, compound 1.2+imazaquin, compound 1.2+imazethapyr, compound 1.2+indaziflam, compound 1.2+iodosulfuron-methyl-sodium, compound 1.2+iofensulfuron, compound 1.2+iofensulfuron-sodium, compound 1.2+ioxynil, compound 1.2+ipfencarbazone, compound 1.2+isoproturon, compound 1.2+isoxaben, compound 1.2+isoxaflutole, compound 1.2+lactofen, compound 1.2+linuron, compound 1.2+MCPA, compound 1.2+MCPP, compound 1.2+mecoprop-P, compound 1.2+mefenacet, compound 1.2+mesosulfuron, compound 1.2+mesosulfuron-methyl, compound 1.2+mesotrione, compound 1.2+metamitron, compound 1.2+metazachlor, compound 1.2+metobromuron, compound 1.2+metolachlor, compound 1.2+metoxuron, compound 1.2+metribuzin, compound 1.2+metsulfuron, compound 1.2+molinate, compound 1.2+napropamide, compound 1.2+nicosulfuron, compound 1.2+norflurazon, compound 1.2+orthosulfamuron, compound 1.2+oxadiargyl, compound 1.2+oxadiazon, compound 1.2+oxasulfuron, compound 1.2+oxyfluorfen, compound 1.2+paraquat dichloride, compound 1.2+pendimethalin, compound 1.2+penoxsulam, compound 1.2+pethoxamid, compound 1.2+phenmedipham, compound 1.2+picloram, compound 1.2+picolinafen, compound 1.2+pinoxaden, compound 1.2+pretilachlor, compound 1.2+primisulfuron-methyl, compound 1.2+prodiamine, compound 1.2+prometryn, compound 1.2+propachlor, compound 1.2+propanil, compound 1.2+propaquizafop, compound 1.2+propham, compound 1.2+propoxycarbazone, compound 1.2+propyzamide, compound 1.2+prosulfocarb, compound 1.2+prosulfuron, compound 1.2+pyrasulfotole, compound 1.2+pyrazolynate, compound 1.2+pyrazosulfuron-ethyl, compound 1.2+pyribenzoxim, compound 1.2+pyridate, compound 1.2+pyriftalid, compound 1.2+pyrithiobac-sodium, compound 1.2+pyroxasulfone, compound 1.2+pyroxsulam, compound 1.2+quinclorac, compound 1.2+quizalofop-P-ethyl, compound 1.2+rimsulfuron, compound 1.2+saflufenacil, compound 1.2+sethoxydim, compound 1.2+S-metolachlor, compound 1.2+sulcotrione, compound 1.2+sulfentrazone, compound 1.2+sulfometuron-methyl, compound 1.2+sulfosulfuron, compound 1.2+tebuthiuron, compound 1.2+tefuryltrione, compound 1.2+tembotrione, compound 1.2+terbuthylazine, compound 1.2+terbutryn, compound 1.2+thiencarbazone, compound 1.2+thifensulfuron, compound 1.2+tiafenacil, compound 1.2+tolpyralate, compound 1.2+topramezone, compound 1.2+tralkoxydim, compound 1.2+triafamone, compound 1.2+triallate, compound 1.2+triasulfuron, compound 1.2+tribenuron-methyl, compound 1.2+triclopyr, compound 1.2+trifloxysulfuron-sodium, compound 1.2+trifludimoxazin, compound 1.2+trifluralin, compound 1.2+tritosulfuron and compound 1.2+4-amino-3-chloro-6-(4-chloro-2-fluoro-3-methoxyphenyl)-5-fluoro-pyridine-2-carboxylate;

compound 1.3+acetochlor, compound 1.3+acifluorfen-sodium, compound 1.3+aclonifen, compound 1.3+alachlor, compound 1.3+alloxydim, compound 1.3+ametryn, compound 1.3+amicarbazone, compound 1.3+amidosulfuron, compound 1.3+aminocyclopyrachlor, compound 1.3+aminopyralid, compound 1.3+amitrole, compound 1.3+asulam, compound 1.3+atrazine, compound 1.3+beflubutamid, compound 1.3+benfluralin, compound 1.3+bensulfuron-methyl, compound 1.3+bentazone, compound 1.3+bicyclopyrone, compound 1.3+bifenox, compound 1.3+bispyribac-sodium, compound 1.3+bromacil, compound 1.3+bromoxynil, compound 1.3+butafenacil, compound 1.3+cafenstrole, compound 1.3+carfentrazone-ethyl, compound 1.3+chloransulam, compound 1.3+chlorimuron-ethyl, compound 1.3+chlorotoluron, compound 1.3+chlorsulfuron, compound 1.3+cinosulfuron, compound 1.3+cinidon-ethyl, compound 1.3+clethodim, compound 1.3+clodinafop-propargyl, compound 1.3+clomazone, compound 1.3+clopyralid, compound 1.3+cycloxydim, compound 1.3+cyhalofop-butyl, compound 1.3+2,4-D (including the choline salt and 2-ethylhexyl ester thereof), compound 1.3+daimuron, compound 1.3+desmedipham, compound 1.3+dicamba (including the aluminum, aminopropyl, bis-aminopropylmethyl, choline, diglycolamine, dimethylamine, dimethylammonium, potassium and sodium salts thereof), compound 1.3+diclofop-methyl, compound 1.3+diclosulam, compound 1.3+difenzoquat, compound 1.3+diflufenican, compound 1.3+diflufenzopyr, compound 1.3+dimethachlor, compound 1.3+dimethenamid-P, compound 1.3+diquat dibromide, compound 1.3+diuron, compound 1.3+esprocarb, compound 1.3+ethametsulfuron, compound 1.3+ethofumesate, compound 1.3+fenoxaprop-P-ethyl, compound 1.3+fenquinotrione, compound 1.3+flazasulfuron, compound 1.3+florasulam, compound 1.3+fluazifop-P-butyl, compound 1.3+flucarbazone-sodium, compound 1.3+flufenacet, compound 1.3+flumetralin, compound 1.3+flumetsulam, compound 1.3+flumioxazin, compound 1.3+flupyrsulfuron-methyl-sodium, compound 1.3+fluroxypyr-meptyl, compound 1.3+flurtamone, compound 1.3+fluthiacet-methyl, compound 1.3+fomesafen, compound 1.3+foramsulfuron, compound 1.3+glufosinate (including the ammonium salt thereof), compound 1.3+glyphosate (including the diammonium, isopropylammonium and potassium salts thereof), compound 1.3+halauxifen-methyl, compound 1.3+halosulfuron-methyl, compound 1.3+haloxyfop-methyl, compound 1.3+hexazinone, compound 1.3+imazamethabenz, compound 1.3+imazamox, compound 1.3+imazapic, compound 1.3+imazapyr, compound 1.3+imazaquin, compound 1.3+imazethapyr, compound 1.3+indaziflam, compound 1.3+iodosulfuron-methyl-sodium, compound 1.3+iofensulfuron, compound 1.3+iofensulfuron-sodium, compound 1.3+ioxynil, compound 1.3+ipfencarbazone, compound 1.3+isoproturon, compound 1.3+isoxaben, compound 1.3+isoxaflutole, compound 1.3+lactofen, compound 1.3+linuron, compound 1.3+MCPA, compound 1.3+MCPP, compound 1.3+mecoprop-P, compound 1.3+mefenacet, compound 1.3+mesosulfuron, compound 1.3+mesosulfuron-methyl, compound 1.3+mesotrione, compound 1.3+metamitron, compound 1.3+metazachlor, compound 1.3+metobromuron, compound 1.3+metolachlor, compound 1.3+metoxuron, compound 1.3+metribuzin, compound 1.3+metsulfuron, compound 1.3+molinate, compound 1.3+napropamide, compound 1.3+nicosulfuron, compound 1.3+norflurazon, compound 1.3+orthosulfamuron, compound 1.3+oxadiargyl, compound 1.3+oxadiazon, compound 1.3+oxasulfuron, compound 1.3+oxyfluorfen, compound 1.3+paraquat dichloride, compound 1.3+pendimethalin, compound 1.3+penoxsulam, compound 1.3+pethoxamid, compound 1.3+phenmedipham, compound 1.3+picloram, compound 1.3+picolinafen, compound 1.3+pinoxaden, compound 1.3+pretilachlor, compound 1.3+primisulfuron-methyl, compound 1.3+prodiamine, compound 1.3+prometryn, compound 1.3+propachlor, compound 1.3+propanil, compound 1.3+propaquizafop, compound 1.3+propham, compound 1.3+propoxycarbazone, compound 1.3+propyzamide, compound 1.3+prosulfocarb, compound 1.3+prosulfuron, compound 1.3+pyrasulfotole, compound 1.3+pyrazolynate, compound 1.3+pyrazosulfuron-ethyl, compound 1.3+pyribenzoxim, compound 1.3+pyridate, compound 1.3+pyriftalid, compound 1.3+pyrithiobac-sodium, compound 1.3+pyroxasulfone, compound 1.3+pyroxsulam, compound 1.3+quinclorac, compound 1.3+quizalofop-P-ethyl, compound 1.3+rimsulfuron, compound 1.3+saflufenacil, compound 1.3+sethoxydim, compound 1.3+S-metolachlor, compound 1.3+sulcotrione, compound 1.3+sulfentrazone, compound 1.3+sulfometuron-methyl, compound 1.3+sulfosulfuron, compound 1.3+tebuthiuron, compound 1.3+tefuryltrione, compound 1.3+tembotrione, compound 1.3+terbuthylazine, compound 1.3+terbutryn, compound 1.3+thiencarbazone, compound 1.3+thifensulfuron, compound 1.3+tiafenacil, compound 1.3+tolpyralate, compound 1.3+topramezone, compound 1.3+tralkoxydim, compound 1.3+triafamone, compound 1.3+triallate, compound 1.3+triasulfuron, compound 1.3+tribenuron-methyl, compound 1.3+triclopyr, compound 1.3+trifloxysulfuron-sodium, compound 1.3+trifludimoxazin, compound 1.3+trifluralin, compound 1.3+tritosulfuron and compound 1.3+4-amino-3-chloro-6-(4-chloro-2-fluoro-3-methoxyphenyl)-5-fluoro-pyridine-2-carboxylate;

compound 1.4+acetochlor, compound 1.4+acifluorfen-sodium, compound 1.4+aclonifen, compound 1.4+alachlor, compound 1.4+alloxydim, compound 1.4+ametryn, compound 1.4+amicarbazone, compound 1.4+amidosulfuron, compound 1.4+aminocyclopyrachlor, compound 1.4+aminopyralid, compound 1.4+amitrole, compound 1.4+asulam, compound 1.4+atrazine, compound 1.4+beflubutamid, compound 1.4+benfluralin, compound 1.4+bensulfuron-methyl, compound 1.4+bentazone, compound 1.4+bicyclopyrone, compound 1.4+bifenox, compound 1.4+bispyribac-sodium, compound 1.4+bromacil, compound 1.4+bromoxynil, compound 1.4+butafenacil, compound 1.4+cafenstrole, compound 1.4+carfentrazone-ethyl, compound 1.4+chloransulam, compound 1.4+chlorimuron-ethyl, compound 1.4+chlorotoluron, compound 1.4+chlorsulfuron, compound 1.4+cinosulfuron, compound 1.4+cinidon-ethyl, compound 1.4+clethodim, compound 1.4+clodinafop-propargyl, compound 1.4+clomazone, compound 1.4+clopyralid, compound 1.4+cycloxydim, compound 1.4+cyhalofop-butyl, compound 1.4+2,4-D (including the choline salt and 2-ethylhexyl ester thereof), compound 1.4+daimuron, compound 1.4+desmedipham, compound 1.4+dicamba (including the aluminum, aminopropyl, bis-aminopropylmethyl, choline, diglycolamine, dimethylamine, dimethylammonium, potassium and sodium salts thereof), compound 1.4+diclofop-methyl, compound 1.4+diclosulam, compound 1.4+difenzoquat, compound 1.4+diflufenican, compound 1.4+diflufenzopyr, compound 1.4+dimethachlor, compound 1.4+dimethenamid-P, compound 1.4+diquat dibromide, compound 1.4+diuron, compound 1.4+esprocarb, compound 1.4+ethametsulfuron, compound 1.4+ethofumesate, compound 1.4+fenoxaprop-P-ethyl, compound 1.4+fenquinotrione, compound 1.4+flazasulfuron, compound 1.4+florasulam, compound 1.4+fluazifop-P-butyl, compound 1.4+flucarbazone-sodium, compound 1.4+flufenacet, compound 1.4+flumetralin, compound 1.4+flumetsulam, compound 1.4+flumioxazin, compound 1.4+flupyrsulfuron-methyl-sodium, compound 1.4+fluroxypyr-meptyl, compound 1.4+flurtamone, compound 1.4+fluthiacet-methyl, compound 1.4+fomesafen, compound 1.4+foramsulfuron, compound 1.4+glufosinate (including the ammonium salt thereof), compound 1.4+glyphosate (including the diammonium, isopropylammonium and potassium salts thereof), compound 1.4+halauxifen-methyl, compound 1.4+halosulfuron-methyl, compound 1.4+haloxyfop-methyl, compound 1.4+hexazinone, compound 1.4+imazamethabenz, compound 1.4+imazamox, compound 1.4+imazapic, compound 1.4+imazapyr, compound 1.4+imazaquin, compound 1.4+imazethapyr, compound 1.4+indaziflam, compound 1.4+iodosulfuron-methyl-sodium, compound 1.4+iofensulfuron, compound 1.4+iofensulfuron-sodium, compound 1.4+ioxynil, compound 1.4+ipfencarbazone, compound 1.4+isoproturon, compound 1.4+isoxaben, compound 1.4+isoxaflutole, compound 1.4+lactofen, compound 1.4+linuron, compound 1.4+MCPA, compound 1.4+MCPP, compound 1.4+mecoprop-P, compound 1.4+mefenacet, compound 1.4+mesosulfuron, compound 1.4+mesosulfuron-methyl, compound 1.4+mesotrione, compound 1.4+metamitron, compound 1.4+metazachlor, compound 1.4+metobromuron, compound 1.4+metolachlor, compound 1.4+metoxuron, compound 1.4+metribuzin, compound 1.4+metsulfuron, compound 1.4+molinate, compound 1.4+napropamide, compound 1.4+nicosulfuron, compound 1.4+norflurazon, compound 1.4+orthosulfamuron, compound 1.4+oxadiargyl, compound 1.4+oxadiazon, compound 1.4+oxasulfuron, compound 1.4+oxyfluorfen, compound 1.4+paraquat dichloride, compound 1.4+pendimethalin, compound 1.4+penoxsulam, compound 1.4+pethoxamid, compound 1.4+phenmedipham, compound 1.4+picloram, compound 1.4+picolinafen, compound 1.4+pinoxaden, compound 1.4+pretilachlor, compound 1.4+primisulfuron-methyl, compound 1.4+prodiamine, compound 1.4+prometryn, compound 1.4+propachlor, compound 1.4+propanil, compound 1.4+propaquizafop, compound 1.4+propham, compound 1.4+propoxycarbazone, compound 1.4+propyzamide, compound 1.4+prosulfocarb, compound 1.4+prosulfuron, compound 1.4+pyrasulfotole, compound 1.4+pyrazolynate, compound 1.4+pyrazosulfuron-ethyl, compound 1.4+pyribenzoxim, compound 1.4+pyridate, compound 1.4+pyriftalid, compound 1.4+pyrithiobac-sodium, compound 1.4+pyroxasulfone, compound 1.4+pyroxsulam, compound 1.4+quinclorac, compound 1.4+quizalofop-P-ethyl, compound 1.4+rimsulfuron, compound 1.4+saflufenacil, compound 1.4+sethoxydim, compound 1.4+S-metolachlor, compound 1.4+sulcotrione, compound 1.4+sulfentrazone, compound 1.4+sulfometuron-methyl, compound 1.4+sulfosulfuron, compound 1.4+tebuthiuron, compound 1.4+tefuryltrione, compound 1.4+tembotrione, compound 1.4+terbuthylazine, compound 1.4+terbutryn, compound 1.4+thiencarbazone, compound 1.4+thifensulfuron, compound 1.4+tiafenacil, compound 1.4+tolpyralate, compound 1.4+topramezone, compound 1.4+tralkoxydim, compound 1.4+triafamone, compound 1.4+triallate, compound 1.4+triasulfuron, compound 1.4+tribenuron-methyl, compound 1.4+triclopyr, compound 1.4+trifloxysulfuron-sodium, compound 1.4+trifludimoxazin, compound 1.4+trifluralin, compound 1.4+tritosulfuron and compound 1.4+4-amino-3-chloro-6-(4-chloro-2-fluoro-3-methoxyphenyl)-5-fluoro-pyridine-2-carboxylate;

compound 1.5+acetochlor, compound 1.5+acifluorfen-sodium, compound 1.5+aclonifen, compound 1.5+alachlor, compound 1.5+alloxydim, compound 1.5+ametryn, compound 1.5+amicarbazone, compound 1.5+amidosulfuron, compound 1.5+aminocyclopyrachlor, compound 1.5+aminopyralid, compound 1.5+amitrole, compound 1.5+asulam, compound 1.5+atrazine, compound 1.5+beflubutamid, compound 1.5+benfluralin, compound 1.5+bensulfuron-methyl, compound 1.5+bentazone, compound 1.5+bicyclopyrone, compound 1.5+bifenox, compound 1.5+bispyribac-sodium, compound 1.5+bromacil, compound 1.5+bromoxynil, compound 1.5+butafenacil, compound 1.5+cafenstrole, compound 1.5+carfentrazone-ethyl, compound 1.5+chloransulam, compound 1.5+chlorimuron-ethyl, compound 1.5+chlorotoluron, compound 1.5+chlorsulfuron, compound 1.5+cinosulfuron, compound 1.5+cinidon-ethyl, compound 1.5+clethodim, compound 1.5+clodinafop-propargyl, compound 1.5+clomazone, compound 1.5+clopyralid, compound 1.5+cycloxydim, compound 1.5+cyhalofop-butyl, compound 1.5+2,4-D (including the choline salt and 2-ethylhexyl ester thereof), compound 1.5+daimuron, compound 1.5+desmedipham, compound 1.5+dicamba (including the aluminum, aminopropyl, bis-aminopropylmethyl, choline, diglycolamine, dimethylamine, dimethylammonium, potassium and sodium salts thereof), compound 1.5+diclofop-methyl, compound 1.5+diclosulam, compound 1.5+difenzoquat, compound 1.5+diflufenican, compound 1.5+diflufenzopyr, compound 1.5+dimethachlor, compound 1.5+dimethenamid-P, compound 1.5+diquat dibromide, compound 1.5+diuron, compound 1.5+esprocarb, compound 1.5+ethametsulfuron, compound 1.5+ethofumesate, compound 1.5+fenoxaprop-P-ethyl, compound 1.5+fenquinotrione, compound 1.5+flazasulfuron, compound 1.5+florasulam, compound 1.5+fluazifop-P-butyl, compound 1.5+flucarbazone-sodium, compound 1.5+flufenacet, compound 1.5+flumetralin, compound 1.5+flumetsulam, compound 1.5+flumioxazin, compound 1.5+flupyrsulfuron-methyl-sodium, compound 1.5+fluroxypyr-meptyl, compound 1.5+flurtamone, compound 1.5+fluthiacet-methyl, compound 1.5+fomesafen, compound 1.5+foramsulfuron, compound 1.5+glufosinate (including the ammonium salt thereof), compound 1.5+glyphosate (including the diammonium, isopropylammonium and potassium salts thereof), compound 1.5+halauxifen-methyl, compound 1.5+halosulfuron-methyl, compound 1.5+haloxyfop-methyl, compound 1.5+hexazinone, compound 1.5+imazamethabenz, compound 1.5+imazamox, compound 1.5+imazapic, compound 1.5+imazapyr, compound 1.5+imazaquin, compound 1.5+imazethapyr, compound 1.5+indaziflam, compound 1.5+iodosulfuron-methyl-sodium, compound 1.5+iofensulfuron, compound 1.5+iofensulfuron-sodium, compound 1.5+ioxynil, compound 1.5+ipfencarbazone, compound 1.5+isoproturon, compound 1.5+isoxaben, compound 1.5+isoxaflutole, compound 1.5+lactofen, compound 1.5+linuron, compound 1.5+MCPA, compound 1.5+MCPP, compound 1.5+mecoprop-P, compound 1.5+mefenacet, compound 1.5+mesosulfuron, compound 1.5+mesosulfuron-methyl, compound 1.5+mesotrione, compound 1.5+metamitron, compound 1.5+metazachlor, compound 1.5+metobromuron, compound 1.5+metolachlor, compound 1.5+metoxuron, compound 1.5+metribuzin, compound 1.5+metsulfuron, compound 1.5+molinate, compound 1.5+napropamide, compound 1.5+nicosulfuron, compound 1.5+norflurazon, compound 1.5+orthosulfamuron, compound 1.5+oxadiargyl, compound 1.5+oxadiazon, compound 1.5+oxasulfuron, compound 1.5+oxyfluorfen, compound 1.5+paraquat dichloride, compound 1.5+pendimethalin, compound 1.5+penoxsulam, compound 1.5+pethoxamid, compound 1.5+phenmedipham, compound 1.5+picloram, compound 1.5+picolinafen, compound 1.5+pinoxaden, compound 1.5+pretilachlor, compound 1.5+primisulfuron-methyl, compound 1.5+prodiamine, compound 1.5+prometryn, compound 1.5+propachlor, compound 1.5+propanil, compound 1.5+propaquizafop, compound 1.5+propham, compound 1.5+propoxycarbazone, compound 1.5+propyzamide, compound 1.5+prosulfocarb, compound 1.5+prosulfuron, compound 1.5+pyrasulfotole, compound 1.5+pyrazolynate, compound 1.5+pyrazosulfuron-ethyl, compound 1.5+pyribenzoxim, compound 1.5+pyridate, compound 1.5+pyriftalid, compound 1.5+pyrithiobac-sodium, compound 1.5+pyroxasulfone, compound 1.5+pyroxsulam, compound 1.5+quinclorac, compound 1.5+quizalofop-P-ethyl, compound 1.5+rimsulfuron, compound 1.5+saflufenacil, compound 1.5+sethoxydim, compound 1.5+S-metolachlor, compound 1.5+sulcotrione, compound 1.5+sulfentrazone, compound 1.5+sulfometuron-methyl, compound 1.5+sulfosulfuron, compound 1.5+tebuthiuron, compound 1.5+tefuryltrione, compound 1.5+tembotrione, compound 1.5+terbuthylazine, compound 1.5+terbutryn, compound 1.5+thiencarbazone, compound 1.5+thifensulfuron, compound 1.5+tiafenacil, compound 1.5+tolpyralate, compound 1.5+topramezone, compound 1.5+tralkoxydim, compound 1.5+triafamone, compound 1.5+triallate, compound 1.5+triasulfuron, compound 1.5+tribenuron-methyl, compound 1.5+triclopyr, compound 1.5+trifloxysulfuron-sodium, compound 1.5+trifludimoxazin, compound 1.5+trifluralin, compound 1.5+tritosulfuron and compound 1.5+4-amino-3-chloro-6-(4-chloro-2-fluoro-3-methoxyphenyl)-5-fluoro-pyridine-2-carboxylate.

Whilst two-way mixtures of a compound of formula (I) and another herbicide are explicitly disclosed above, the skilled man will appreciate that the invention extends to three-way and further multiple combinations comprising the above two-way mixtures. In particular, the present invention provides compositions comprising the three-way mixtures listed in Table 1 below:

TABLE 1

| Compound of formula (I) | Mixing Partner 1 | Mixing Partner 2 |
| --- | --- | --- |
| 1.1 | Mesotrione | Bicyclopyrone |
| 1.1 | Mesotrione | Atrazine |
| 1.1 | Mesotrione | S-metolachlor |
| 1.1 | Mesotrione | Terbuthylazine |
| 1.1 | Mesotrione | Dimethachlor |
| 1.1 | Mesotrione | Flufenacet |
| 1.1 | Mesotrione | Glyphosate |
| 1.1 | Mesotrione | Isoxaflutole |
| 1.1 | Mesotrione | Nicosulfuron |
| 1.1 | Mesotrione | Ametryn |
| 1.1 | Mesotrione | Hexazinone |
| 1.1 | Mesotrione | Paraquat |
| 1.1 | Mesotrione | Diquat |

TABLE 1-continued

| Compound of formula (I) | Mixing Partner 1 | Mixing Partner 2 |
| --- | --- | --- |
| 1.1 | Mesotrione | Pyridate |
| 1.1 | Mesotrione | Acetochlor |
| 1.1 | Mesotrione | Dimethenamid-P |
| 1.1 | Mesotrione | Pendimethalin |
| 1.1 | Mesotrione | Alachlor |
| 1.1 | Mesotrione | Pethoxamid |
| 1.1 | Mesotrione | Pyroxasulfone |
| 1.1 | Mesotrione | Trifloxysulfuron-sodium |
| 1.1 | Mesotrione | Flazasulfuron |
| 1.1 | Mesotrione | Prosulfocarb |
| 1.1 | Mesotrione | Metolachlor |
| 1.1 | Bicyclopyrone | Atrazine |
| 1.1 | Bicyclopyrone | S-metolachlor |
| 1.1 | Bicyclopyrone | Terbuthylazine |
| 1.1 | Bicyclopyrone | Dimethachlor |
| 1.1 | Bicyclopyrone | Flufenacet |
| 1.1 | Bicyclopyrone | Glyphosate |
| 1.1 | Bicyclopyrone | Isoxaflutole |
| 1.1 | Bicyclopyrone | Nicosulfuron |
| 1.1 | Bicyclopyrone | Ametryn |
| 1.1 | Bicyclopyrone | Hexazinone |
| 1.1 | Bicyclopyrone | Paraquat |
| 1.1 | Bicyclopyrone | Diquat |
| 1.1 | Bicyclopyrone | Pyridate |
| 1.1 | Bicyclopyrone | Acetochlor |
| 1.1 | Bicyclopyrone | Dimethenamid-P |
| 1.1 | Bicyclopyrone | Pendimethalin |
| 1.1 | Bicyclopyrone | Alachlor |
| 1.1 | Bicyclopyrone | Pethoxamid |
| 1.1 | Bicyclopyrone | Pyroxasulfone |
| 1.1 | Bicyclopyrone | Trifloxysulfuron-sodium |
| 1.1 | Bicyclopyrone | Flazasulfuron |
| 1.1 | Bicyclopyrone | Prosulfocarb |
| 1.1 | Bicyclopyrone | Metolachlor |
| 1.1 | Atrazine | S-metolachlor |
| 1.1 | Atrazine | Terbuthylazine |
| 1.1 | Atrazine | Dimethachlor |
| 1.1 | Atrazine | Flufenacet |
| 1.1 | Atrazine | Glyphosate |
| 1.1 | Atrazine | Isoxaflutole |
| 1.1 | Atrazine | Nicosulfuron |
| 1.1 | Atrazine | Ametryn |
| 1.1 | Atrazine | Hexazinone |
| 1.1 | Atrazine | Paraquat |
| 1.1 | Atrazine | Diquat |
| 1.1 | Atrazine | Pyridate |
| 1.1 | Atrazine | Acetochlor |
| 1.1 | Atrazine | Dimethenamid-P |
| 1.1 | Atrazine | Pendimethalin |
| 1.1 | Atrazine | Alachlor |
| 1.1 | Atrazine | Pethoxamid |
| 1.1 | Atrazine | Pyroxasulfone |
| 1.1 | Atrazine | Trifloxysulfuron-sodium |
| 1.1 | Atrazine | Flazasulfuron |
| 1.1 | Atrazine | Prosulfocarb |
| 1.1 | Atrazine | Metolachlor |
| 1.1 | S-metolachlor | Terbuthylazine |
| 1.1 | S-metolachlor | Dimethachlor |
| 1.1 | S-metolachlor | Flufenacet |
| 1.1 | S-metolachlor | Glyphosate |
| 1.1 | S-metolachlor | Isoxaflutole |
| 1.1 | S-metolachlor | Nicosulfuron |
| 1.1 | S-metolachlor | Ametryn |
| 1.1 | S-metolachlor | Hexazinone |
| 1.1 | S-metolachlor | Paraquat |
| 1.1 | S-metolachlor | Diquat |
| 1.1 | S-metolachlor | Pyridate |
| 1.1 | S-metolachlor | Acetochlor |
| 1.1 | S-metolachlor | Dimethenamid-P |
| 1.1 | S-metolachlor | Pendimethalin |
| 1.1 | S-metolachlor | Alachlor |
| 1.1 | S-metolachlor | Pethoxamid |
| 1.1 | S-metolachlor | Pyroxasulfone |
| 1.1 | S-metolachlor | Trifloxysulfuron-sodium |
| 1.1 | S-metolachlor | Flazasulfuron |
| 1.1 | S-metolachlor | Prosulfocarb |
| 1.1 | S-metolachlor | Metolachlor |

TABLE 1-continued

| Compound of formula (I) | Mixing Partner 1 | Mixing Partner 2 |
|---|---|---|
| 1.1 | Terbuthylazine | Dimethachlor |
| 1.1 | Terbuthylazine | Flufenacet |
| 1.1 | Terbuthylazine | Glyphosate |
| 1.1 | Terbuthylazine | Isoxaflutole |
| 1.1 | Terbuthylazine | Nicosulfuron |
| 1.1 | Terbuthylazine | Ametryn |
| 1.1 | Terbuthylazine | Hexazinone |
| 1.1 | Terbuthylazine | Paraquat |
| 1.1 | Terbuthylazine | Diquat |
| 1.1 | Terbuthylazine | Pyridate |
| 1.1 | Terbuthylazine | Acetochlor |
| 1.1 | Terbuthylazine | Dimethenamid-P |
| 1.1 | Terbuthylazine | Pendimethalin |
| 1.1 | Terbuthylazine | Alachlor |
| 1.1 | Terbuthylazine | Pethoxamid |
| 1.1 | Terbuthylazine | Pyroxasulfone |
| 1.1 | Terbuthylazine | Trifloxysulfuron-sodium |
| 1.1 | Terbuthylazine | Flazasulfuron |
| 1.1 | Terbuthylazine | Prosulfocarb |
| 1.1 | Terbuthylazine | Metolachlor |
| 1.1 | Dimethachlor | Flufenacet |
| 1.1 | Dimethachlor | Glyphosate |
| 1.1 | Dimethachlor | Isoxaflutole |
| 1.1 | Dimethachlor | Nicosulfuron |
| 1.1 | Dimethachlor | Ametryn |
| 1.1 | Dimethachlor | Hexazinone |
| 1.1 | Dimethachlor | Paraquat |
| 1.1 | Dimethachlor | Diquat |
| 1.1 | Dimethachlor | Pyridate |
| 1.1 | Dimethachlor | Acetochlor |
| 1.1 | Dimethachlor | Dimethenamid-P |
| 1.1 | Dimethachlor | Pendimethalin |
| 1.1 | Dimethachlor | Alachlor |
| 1.1 | Dimethachlor | Pethoxamid |
| 1.1 | Dimethachlor | Pyroxasulfone |
| 1.1 | Dimethachlor | Trifloxysulfuron-sodium |
| 1.1 | Dimethachlor | Flazasulfuron |
| 1.1 | Dimethachlor | Prosulfocarb |
| 1.1 | Dimethachlor | Metolachlor |
| 1.1 | Flufenacet | Glyphosate |
| 1.1 | Flufenacet | Isoxaflutole |
| 1.1 | Flufenacet | Nicosulfuron |
| 1.1 | Flufenacet | Ametryn |
| 1.1 | Flufenacet | Hexazinone |
| 1.1 | Flufenacet | Paraquat |
| 1.1 | Flufenacet | Diquat |
| 1.1 | Flufenacet | Pyridate |
| 1.1 | Flufenacet | Acetochlor |
| 1.1 | Flufenacet | Dimethenamid-P |
| 1.1 | Flufenacet | Pendimethalin |
| 1.1 | Flufenacet | Alachlor |
| 1.1 | Flufenacet | Pethoxamid |
| 1.1 | Flufenacet | Pyroxasulfone |
| 1.1 | Flufenacet | Trifloxysulfuron-sodium |
| 1.1 | Flufenacet | Flazasulfuron |
| 1.1 | Flufenacet | Prosulfocarb |
| 1.1 | Flufenacet | Metolachlor |
| 1.1 | Glyphosate | Isoxaflutole |
| 1.1 | Glyphosate | Nicosulfuron |
| 1.1 | Glyphosate | Ametryn |
| 1.1 | Glyphosate | Hexazinone |
| 1.1 | Glyphosate | Paraquat |
| 1.1 | Glyphosate | Diquat |
| 1.1 | Glyphosate | Pyridate |
| 1.1 | Glyphosate | Acetochlor |
| 1.1 | Glyphosate | Dimethenamid-P |
| 1.1 | Glyphosate | Pendimethalin |
| 1.1 | Glyphosate | Alachlor |
| 1.1 | Glyphosate | Pethoxamid |
| 1.1 | Glyphosate | Pyroxasulfone |
| 1.1 | Glyphosate | Trifloxysulfuron-sodium |
| 1.1 | Glyphosate | Flazasulfuron |
| 1.1 | Glyphosate | Prosulfocarb |
| 1.1 | Glyphosate | Metolachlor |
| 1.1 | Isoxaflutole | Nicosulfuron |
| 1.1 | Isoxaflutole | Ametryn |
| 1.1 | Isoxaflutole | Hexazinone |
| 1.1 | Isoxaflutole | Paraquat |
| 1.1 | Isoxaflutole | Diquat |
| 1.1 | Isoxaflutole | Pyridate |
| 1.1 | Isoxaflutole | Acetochlor |
| 1.1 | Isoxaflutole | Dimethenamid-P |
| 1.1 | Isoxaflutole | Pendimethalin |
| 1.1 | Isoxaflutole | Alachlor |
| 1.1 | Isoxaflutole | Pethoxamid |
| 1.1 | Isoxaflutole | Pyroxasulfone |
| 1.1 | Isoxaflutole | Trifloxysulfuron-sodium |
| 1.1 | Isoxaflutole | Flazasulfuron |
| 1.1 | Isoxaflutole | Prosulfocarb |
| 1.1 | Isoxaflutole | Metolachlor |
| 1.1 | Nicosulfuron | Ametryn |
| 1.1 | Nicosulfuron | Hexazinone |
| 1.1 | Nicosulfuron | Paraquat |
| 1.1 | Nicosulfuron | Diquat |
| 1.1 | Nicosulfuron | Pyridate |
| 1.1 | Nicosulfuron | Acetochlor |
| 1.1 | Nicosulfuron | Dimethenamid-P |
| 1.1 | Nicosulfuron | Pendimethalin |
| 1.1 | Nicosulfuron | Alachlor |
| 1.1 | Nicosulfuron | Pethoxamid |
| 1.1 | Nicosulfuron | Pyroxasulfone |
| 1.1 | Nicosulfuron | Trifloxysulfuron-sodium |
| 1.1 | Nicosulfuron | Flazasulfuron |
| 1.1 | Nicosulfuron | Prosulfocarb |
| 1.1 | Nicosulfuron | Metolachlor |
| 1.1 | Ametryn | Hexazinone |
| 1.1 | Ametryn | Paraquat |
| 1.1 | Ametryn | Diquat |
| 1.1 | Ametryn | Pyridate |
| 1.1 | Ametryn | Acetochlor |
| 1.1 | Ametryn | Dimethenamid-P |
| 1.1 | Ametryn | Pendimethalin |
| 1.1 | Ametryn | Alachlor |
| 1.1 | Ametryn | Pethoxamid |
| 1.1 | Ametryn | Pyroxasulfone |
| 1.1 | Ametryn | Trifloxysulfuron-sodium |
| 1.1 | Ametryn | Flazasulfuron |
| 1.1 | Ametryn | Prosulfocarb |
| 1.1 | Ametryn | Metolachlor |
| 1.1 | Hexazinone | Paraquat |
| 1.1 | Hexazinone | Diquat |
| 1.1 | Hexazinone | Pyridate |
| 1.1 | Hexazinone | Acetochlor |
| 1.1 | Hexazinone | Dimethenamid-P |
| 1.1 | Hexazinone | Pendimethalin |
| 1.1 | Hexazinone | Alachlor |
| 1.1 | Hexazinone | Pethoxamid |
| 1.1 | Hexazinone | Pyroxasulfone |
| 1.1 | Hexazinone | Trifloxysulfuron-sodium |
| 1.1 | Hexazinone | Flazasulfuron |
| 1.1 | Hexazinone | Prosulfocarb |
| 1.1 | Hexazinone | Metolachlor |
| 1.1 | Paraquat | Diquat |
| 1.1 | Paraquat | Pyridate |
| 1.1 | Paraquat | Acetochlor |
| 1.1 | Paraquat | Dimethenamid-P |
| 1.1 | Paraquat | Pendimethalin |
| 1.1 | Paraquat | Alachlor |
| 1.1 | Paraquat | Pethoxamid |
| 1.1 | Paraquat | Pyroxasulfone |
| 1.1 | Paraquat | Trifloxysulfuron-sodium |
| 1.1 | Paraquat | Flazasulfuron |
| 1.1 | Paraquat | Prosulfocarb |
| 1.1 | Paraquat | Metolachlor |
| 1.1 | Diquat | Pyridate |
| 1.1 | Diquat | Acetochlor |
| 1.1 | Diquat | Dimethenamid-P |
| 1.1 | Diquat | Pendimethalin |
| 1.1 | Diquat | Alachlor |
| 1.1 | Diquat | Pethoxamid |
| 1.1 | Diquat | Pyroxasulfone |
| 1.1 | Diquat | Trifloxysulfuron-sodium |
| 1.1 | Diquat | Flazasulfuron |
| 1.1 | Diquat | Prosulfocarb |

TABLE 1-continued

| Compound of formula (I) | Mixing Partner 1 | Mixing Partner 2 |
|---|---|---|
| 1.1 | Diquat | Metolachlor |
| 1.1 | Pyridate | Acetochlor |
| 1.1 | Pyridate | Dimethenamid-P |
| 1.1 | Pyridate | Pendimethalin |
| 1.1 | Pyridate | Alachlor |
| 1.1 | Pyridate | Pethoxamid |
| 1.1 | Pyridate | Pyroxasulfone |
| 1.1 | Pyridate | Trifloxysulfuron-sodium |
| 1.1 | Pyridate | Flazasulfuron |
| 1.1 | Pyridate | Prosulfocarb |
| 1.1 | Pyridate | Metolachlor |
| 1.1 | Acetochlor | Dimethenamid-P |
| 1.1 | Acetochlor | Pendimethalin |
| 1.1 | Acetochlor | Alachlor |
| 1.1 | Acetochlor | Pethoxamid |
| 1.1 | Acetochlor | Pyroxasulfone |
| 1.1 | Acetochlor | Trifloxysulfuron-sodium |
| 1.1 | Acetochlor | Flazasulfuron |
| 1.1 | Acetochlor | Prosulfocarb |
| 1.1 | Acetochlor | Metolachlor |
| 1.1 | Dimethenamid-P | Pendimethalin |
| 1.1 | Dimethenamid-P | Alachlor |
| 1.1 | Dimethenamid-P | Pethoxamid |
| 1.1 | Dimethenamid-P | Pyroxasulfone |
| 1.1 | Dimethenamid-P | Trifloxysulfuron-sodium |
| 1.1 | Dimethenamid-P | Flazasulfuron |
| 1.1 | Dimethenamid-P | Prosulfocarb |
| 1.1 | Dimethenamid-P | Metolachlor |
| 1.1 | Pendimethalin | Alachlor |
| 1.1 | Pendimethalin | Pethoxamid |
| 1.1 | Pendimethalin | Pyroxasulfone |
| 1.1 | Pendimethalin | Trifloxysulfuron-sodium |
| 1.1 | Pendimethalin | Flazasulfuron |
| 1.1 | Pendimethalin | Prosulfocarb |
| 1.1 | Pendimethalin | Metolachlor |
| 1.1 | Alachlor | Pethoxamid |
| 1.1 | Alachlor | Pyroxasulfone |
| 1.1 | Alachlor | Trifloxysulfuron-sodium |
| 1.1 | Alachlor | Flazasulfuron |
| 1.1 | Alachlor | Prosulfocarb |
| 1.1 | Alachlor | Metolachlor |
| 1.1 | Pethoxamid | Pyroxasulfone |
| 1.1 | Pethoxamid | Trifloxysulfuron-sodium |
| 1.1 | Pethoxamid | Flazasulfuron |
| 1.1 | Pethoxamid | Prosulfocarb |
| 1.1 | Pethoxamid | Metolachlor |
| 1.1 | Pyroxasulfone | Trifloxysulfuron-sodium |
| 1.1 | Pyroxasulfone | Flazasulfuron |
| 1.1 | Pyroxasulfone | Prosulfocarb |
| 1.1 | Pyroxasulfone | Metolachlor |
| 1.1 | Trifloxysulfuron-sodium | Flazasulfuron |
| 1.1 | Trifloxysulfuron-sodium | Prosulfocarb |
| 1.1 | Trifloxysulfuron-sodium | Metolachlor |
| 1.1 | Flazasulfuron | Prosulfocarb |
| 1.1 | Flazasulfuron | Metolachlor |
| 1.1 | Prosulfocarb | Metolachlor |

Furthermore, the present invention also provides compositions comprising the three-way mixtures listed in Table 1 above, wherein the compound 1.1 is replaced with compound 1.2.

Furthermore, the present invention also provides compositions comprising the three-way mixtures listed in Table 1 above, wherein the compound 1.1 is replaced with compound 1.3.

Furthermore, the present invention also provides compositions comprising the three-way mixtures listed in Table 1 above, wherein the compound 1.1 is replaced with compound 1.4.

Furthermore, the present invention also provides compositions comprising the three-way mixtures listed in Table 1 above, wherein the compound 1.1 is replaced with compound 1.5.

Particularly preferred three-way mixtures are listed below:

(i) A compound of formula (I) as defined above, mesotrione and bicyclopyrone;

(ii) A compound of formula (I) as defined above, mesotrione and S-metolachlor;

(iii) A compound of formula (I) as defined above, mesotrione and nicosulfuron;

(iv) A compound of formula (I) as defined above, mesotrione and glyphosate;

(v) A compound of formula (I) as defined above, bicyclopyrone and S-metolachlor;

(vi) A compound of formula (I) as defined above, S-metolachlor and isoxaflutole;

(vii) A compound of formula (I) as defined above, S-metolachlor and flufenacet;

(viii) A compound of formula (I) as defined above, S-metolachlor and dimethachlor;

(ix) A compound of formula (I) as defined above, S-metolachlor and glyphosate.

The compositions of the invention can further include one or more safeners. In particular, the following safeners are particularly preferred: AD 67 (MON 4660), benoxacor, cloquintocet-mexyl, cyometrinil, cyprosulfamide, dichlormid, dicyclonon, dietholate, fenchlorazole-ethyl, fenclorim, flurazole, fluxofenim, furilazole, furilazome, isoxadifen-ethyl, mefenpyr-diethyl, mephenate, oxabetrinil, naphthalic anhydride (CAS RN 81-84-5), TI-35, N-isopropyl-4-(2-methoxy-benzoylsulfamoyl)-benzamide (CAS RN 221668-34-4) and N-(2-methoxybenzoyl)-4-[(methylaminocarbonyl)amino]benzenesulfonamide.

Particularly preferred safeners are cloquintocet-mexyl, cyprosulfamide, isoxadifen-ethyl, mefenpyr-diethyl and N-(2-methoxybenzoyl)-4-[(methylaminocarbonyl)amino] benzenesulfonamide.

Preferred compositions of the invention and safeners include:

compound 1.1, S-metolachlor and cloquintocet-mexyl, compound 1.1, S-metolachlor and cyprosulfamide, compound 1.1, S-metolachlor and isoxadifen-ethyl, compound 1.1, S-metolachlor and mefenpyr-diethyl, compound 1.1, S-metolachlor and N-(2-methoxybenzoyl)-4-[(methylaminocarbonyl)amino]benzenesulfonamide;

compound 1.1, mesotrione and cloquintocet-mexyl, compound 1.1, mesotrione and cyprosulfamide, compound 1.1, mesotrione and isoxadifen-ethyl, compound 1.1, mesotrione and mefenpyr-diethyl, compound 1.1, mesotrione and N-(2-methoxybenzoyl)-4-[(methylaminocarbonyl)amino]benzenesulfonamide;

compound 1.1, bicyclopyrone and cloquintocet-mexyl, compound 1.1, bicyclopyrone and cyprosulfamide, compound 1.1, bicyclopyrone and isoxadifen-ethyl, compound 1.1, bicyclopyrone and mefenpyr-diethyl, compound 1.1, bicyclopyrone and N-(2-methoxybenzoyl)-4-[(methylaminocarbonyl)amino]benzenesulfonamide;

compound 1.1, atrazine and cloquintocet-mexyl, compound 1.1, atrazine and cyprosulfamide, compound 1.1, atrazine and isoxadifen-ethyl, compound 1.1, atrazine and mefenpyr-diethyl, compound 1.1, atrazine and N-(2-methoxybenzoyl)-4-[(methylaminocarbonyl)amino]benzenesulfonamide;

compound 1.1, terbuthylazine and cloquintocet-mexyl, compound 1.1, terbuthylazine and cyprosulfamide, compound 1.1, terbuthylazine and isoxadifen-ethyl, compound 1.1, terbuthylazine and mefenpyr-diethyl, compound 1.1, terbuthylazine and N-(2-methoxybenzoyl)-4-[(methylaminocarbonyl)amino]benzenesulfonamide;

compound 1.2, S-metolachlor and cloquintocet-mexyl, compound 1.2, S-metolachlor and cyprosulfamide, compound 1.2, S-metolachlor and isoxadifen-ethyl, compound 1.2, S-metolachlor and mefenpyr-diethyl, compound 1.2, S-metolachlor and N-(2-methoxybenzoyl)-4-[(methylaminocarbonyl)amino]benzenesulfonamide;

compound 1.2, mesotrione and cloquintocet-mexyl, compound 1.2, mesotrione and cyprosulfamide, compound 1.2, mesotrione and isoxadifen-ethyl, compound 1.2, mesotrione and mefenpyr-diethyl, compound 1.2, mesotrione and N-(2-methoxybenzoyl)-4-[(methylaminocarbonyl)amino]benzenesulfonamide;

compound 1.2, bicyclopyrone and cloquintocet-mexyl, compound 1.2, bicyclopyrone and cyprosulfamide, compound 1.2, bicyclopyrone and isoxadifen-ethyl, compound 1.2, bicyclopyrone and mefenpyr-diethyl, compound 1.2, bicyclopyrone and N-(2-methoxybenzoyl)-4-[(methylaminocarbonyl)amino]benzenesulfonamide;

compound 1.2, atrazine and cloquintocet-mexyl, compound 1.2, atrazine and cyprosulfamide, compound 1.2, atrazine and isoxadifen-ethyl, compound 1.2, atrazine and mefenpyr-diethyl, compound 1.2, atrazine and N-(2-methoxybenzoyl)-4-[(methylaminocarbonyl)amino]benzenesulfonamide;

compound 1.2, terbuthylazine and cloquintocet-mexyl, compound 1.2, terbuthylazine and cyprosulfamide, compound 1.2, terbuthylazine and isoxadifen-ethyl, compound 1.2, terbuthylazine and mefenpyr-diethyl, compound 1.2, terbuthylazine and N-(2-methoxybenzoyl)-4-[(methylaminocarbonyl)amino]benzenesulfonamide;

compound 1.3, S-metolachlor and cloquintocet-mexyl, compound 1.3, S-metolachlor and cyprosulfamide, compound 1.3, S-metolachlor and isoxadifen-ethyl, compound 1.3, S-metolachlor and mefenpyr-diethyl, compound 1.3, S-metolachlor and N-(2-methoxybenzoyl)-4-[(methylaminocarbonyl)amino]benzenesulfonamide;

compound 1.3, mesotrione and cloquintocet-mexyl, compound 1.3, mesotrione and cyprosulfamide, compound 1.3, mesotrione and isoxadifen-ethyl, compound 1.3, mesotrione and mefenpyr-diethyl, compound 1.3, mesotrione and N-(2-methoxybenzoyl)-4-[(methylaminocarbonyl)amino]benzenesulfonamide;

compound 1.3, bicyclopyrone and cloquintocet-mexyl, compound 1.3, bicyclopyrone and cyprosulfamide, compound 1.3, bicyclopyrone and isoxadifen-ethyl, compound 1.3, bicyclopyrone and mefenpyr-diethyl, compound 1.3, bicyclopyrone and N-(2-methoxybenzoyl)-4-[(methylaminocarbonyl)amino]benzenesulfonamide;

compound 1.3, atrazine and cloquintocet-mexyl, compound 1.3, atrazine and cyprosulfamide, compound 1.3, atrazine and isoxadifen-ethyl, compound 1.3, atrazine and mefenpyr-diethyl, compound 1.3, atrazine and N-(2-methoxybenzoyl)-4-[(methylaminocarbonyl)amino]benzenesulfonamide;

compound 1.3, terbuthylazine and cloquintocet-mexyl, compound 1.3, terbuthylazine and cyprosulfamide, compound 1.3, terbuthylazine and isoxadifen-ethyl, compound 1.3, terbuthylazine and mefenpyr-diethyl, compound 1.3, terbuthylazine and N-(2-methoxybenzoyl)-4-[(methylaminocarbonyl)amino]benzenesulfonamide;

compound 1.4, S-metolachlor and cloquintocet-mexyl, compound 1.4, S-metolachlor and cyprosulfamide, compound 1.4, S-metolachlor and isoxadifen-ethyl, compound 1.4, S-metolachlor and mefenpyr-diethyl, compound 1.4, S-metolachlor and N-(2-methoxybenzoyl)-4-[(methylaminocarbonyl)amino]benzenesulfonamide;

compound 1.4, mesotrione and cloquintocet-mexyl, compound 1.4, mesotrione and cyprosulfamide, compound 1.4, mesotrione and isoxadifen-ethyl, compound 1.4, mesotrione and mefenpyr-diethyl, compound 1.4, mesotrione and N-(2-methoxybenzoyl)-4-[(methylaminocarbonyl)amino]benzenesulfonamide;

compound 1.4, bicyclopyrone and cloquintocet-mexyl, compound 1.4, bicyclopyrone and cyprosulfamide, compound 1.4, bicyclopyrone and isoxadifen-ethyl, compound 1.4, bicyclopyrone and mefenpyr-diethyl, compound 1.4, bicyclopyrone and N-(2-methoxybenzoyl)-4-[(methylaminocarbonyl)amino]benzenesulfonamide;

compound 1.4, atrazine and cloquintocet-mexyl, compound 1.4, atrazine and cyprosulfamide, compound 1.4, atrazine and isoxadifen-ethyl, compound 1.4, atrazine and mefenpyr-diethyl, compound 1.4, atrazine and N-(2-methoxybenzoyl)-4-[(methylaminocarbonyl)amino]benzenesulfonamide;

compound 1.4, terbuthylazine and cloquintocet-mexyl, compound 1.4, terbuthylazine and cyprosulfamide, compound 1.4, terbuthylazine and isoxadifen-ethyl, compound 1.4, terbuthylazine and mefenpyr-diethyl, compound 1.4, terbuthylazine and N-(2-methoxybenzoyl)-4-[(methylaminocarbonyl)amino]benzenesulfonamide;

compound 1.5, S-metolachlor and cloquintocet-mexyl, compound 1.5, S-metolachlor and cyprosulfamide, compound 1.5, S-metolachlor and isoxadifen-ethyl, compound 1.5, S-metolachlor and mefenpyr-diethyl, compound 1.5, S-metolachlor and N-(2-methoxybenzoyl)-4-[(methylaminocarbonyl)amino]benzenesulfonamide;

compound 1.5, mesotrione and cloquintocet-mexyl, compound 1.5, mesotrione and cyprosulfamide, compound 1.5, mesotrione and isoxadifen-ethyl, compound 1.5, mesotrione and mefenpyr-diethyl, compound 1.5, mesotrione and N-(2-methoxybenzoyl)-4-[(methylaminocarbonyl)amino]benzenesulfonamide;

compound 1.5, bicyclopyrone and cloquintocet-mexyl, compound 1.5, bicyclopyrone and cyprosulfamide, compound 1.5, bicyclopyrone and isoxadifen-ethyl, compound 1.5, bicyclopyrone and mefenpyr-diethyl, compound 1.5, bicyclopyrone and N-(2-methoxybenzoyl)-4-[(methylaminocarbonyl)amino]benzenesulfonamide;

compound 1.5, atrazine and cloquintocet-mexyl, compound 1.5, atrazine and cyprosulfamide, compound 1.5, atrazine and isoxadifen-ethyl, compound 1.5, atrazine and mefenpyr-diethyl, compound 1.5, atrazine and N-(2-methoxybenzoyl)-4-[(methylaminocarbonyl)amino]benzenesulfonamide;

compound 1.5, terbuthylazine and cloquintocet-mexyl, compound 1.5, terbuthylazine and cyprosulfamide, compound 1.5, terbuthylazine and isoxadifen-ethyl, compound 1.5, terbuthylazine and mefenpyr-diethyl, compound 1.5, terbuthylazine and N-(2-methoxybenzoyl)-4-[(methylaminocarbonyl)amino]benzenesulfonamide.

Safeners can also be used in the three-way compositions detailed above and, in addition, in further multiple combinations comprising the two-way mixtures.

The compounds (A) may exist as different geometric isomers, or in different tautomeric forms. This invention covers all such isomers and tautomers, and mixtures thereof in all proportions, as well as isotopic forms such as deuterated compounds. They may contain one or more asymmetric centers and may thus give rise to optical isomers and diastereomers. While shown without respect to stereochemistry, the present invention includes all such optical isomers and diastereomers as well as the racemic and resolved, enantiomerically pure R and S stereoisomers and other mixtures of the R and S stereoisomers and agrochemically acceptable salts thereof. It is recognized certain optical isomers or diastereomers may have favorable properties over the other. Thus when disclosing and claiming the invention, when a racemic mixture is disclosed, it is clearly contemplated that both optical isomers, including diastereomers, substantially free of the other, are disclosed and claimed as well.

Suitable salts include those derived from alkali or alkaline earth metals and those derived from ammonia and amines. Preferred cations include sodium, potassium, magnesium, and ammonium cations of the formula $N^+(R^{19}R^{20}R^{21}R^{22})$ wherein $R^{19}$, $R^{20}$, $R^{21}$ and $R^{22}$ are independently selected from hydrogen, $C_1$-$C_6$ alkyl and $C_1$-$C_6$ hydroxyalkyl. Salts of the compounds of formula (I) can be prepared by treatment of compounds of formula (I) with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of formula (I) because they are water-soluble and lend themselves to the preparation of desirable aqueous based herbicidal compositions.

Acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety.

Compounds 1.1 to 1.5 of the invention may be prepared by techniques detailed in WO 2014/180740, WO 2015/018431, WO 2015/018433 and WO 2015/018434.

Herbicides of component (B) referred to herein using their common name are known, for example, from "The Pesticide Manual", 15th Ed., British Crop Protection Council 2009. As noted in The Pesticide Manual, the herbicides (B) may also be in the form of esters or salts. Thus, the reference to acifluorfen-sodium also applies to acifluorfen, the reference to dimethenamid also applies to dimethenamid-P, the reference to glufosinate-ammonium also applies to glufosinate, the reference to bensulfuron-methyl also applies to bensulfuron, the reference to cloransulam-methyl also applies to cloransulam, the reference to flamprop-M also applies to flamprop, and the reference to pyrithiobac-sodium also applies to pyrithiobac, etc.

The safeners of the compositions of the invention may also be in the form of esters or salts, as mentioned e.g. in The Pesticide Manual, 15th Ed. (BCPC), 2009. Thus, the reference to cloquintocet-mexyl also applies to cloquintocet and to a lithium, sodium, potassium, calcium, magnesium, aluminium, iron, ammonium, quaternary ammonium, sulfonium or phosphonium salt thereof as disclosed in WO02/34048 and the reference to fenchlorazole-ethyl also applies to fenchlorazole, etc.

The compositions according to the invention are generally formulated in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, micro-emulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octa-decanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The formulations according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The formulations generally comprise from 0.1 to 99% by weight, especially from 0.1 to 95% by weight, of compounds (A) and (B) and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%
The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulphate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |

-continued

| Emulsifiable concentrate | |
|---|---|
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruded granules | |
|---|---|
| Active ingredients | 15% |
| sodium lignosulfonate | 2% |
| Carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Throughout this document the expression "composition" stands for the various mixtures or combinations of components (A) and (B), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components (A) and (B) is not essential for working the present invention.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example killing, retardation, leaf burn, albinism, dwarfing and the like.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

The term "safener" as used herein means a chemical that when used in combination with a herbicide reduces the undesirable effects of the herbicide on non-target organisms, for example, a safener protects crops from injury by herbicides but does not prevent the herbicide from killing the weeds.

Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Compositions of the invention can typically be used to control a wide variety of monocotyledonous and dicotyledonous weed species. Examples of monocotyledonous species that can typically be controlled include *Alopecurus myosuroides, Avena fatua, Brachiaria plantaginea, Bromus tectorum, Cyperus esculentus, Digitaria sanguinalis, Echinochloa crus-galli, Lolium perenne, Lolium multiflorum, Panicum miliaceum, Poa annus, Setaria viridis, Setaria faberi* and *Sorghum bicolor*. Examples of dicotyledonous species that can be controlled include *Abutilon theophrasti, Amaranthus retroflexus, Bidens pilosa, Chenopodium album, Euphorbia heterophylla, Galium aparine, Ipomoea hederacea, Kochia scoparia, Polygonum convolvulus, Sida spinosa, Sinapis arvensis, Solanum nigrum, Stellaria media, Veronica persica* and *Xanthium strumarium*.

In all aspects of the invention, in particular embodiment, the weeds, e.g. to be controlled and/or growth-inhibited may be monocotyledonous or dicotyledonous weeds, which are tolerant or resistant to one or more other herbicides for example, HPPD inhibitor herbicides such as mesotrione, PSII inhibitor herbicides such as atrazine or EPSPS inhibitors such as glyphosate. Such weeds include, but are not limited to resistant *Amaranthus* biotypes.

Compositions of this invention can also be mixed with one or more further pesticides including fungicides, insecticides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection.

The compositions of the invention can advantageously be used in the above-mentioned formulations (in which case "active ingredient" relates to the respective mixture of compound of formula (I) with the herbicide (B) or, when a safener is also used, the respective mixture of the compound of formula (I) with the herbicide (B) and the safener).

In general, the mixing ratio (by weight) of the compound of formula (I) to the herbicide (B) is from 0.01:1 to 100:1, more preferably from 0.05:1 to 20:1, even more preferably from 0.1:1 to 20:1 and most preferably from 0.2:1 to 20:1, for example, 0.3125:1, 0.625:1, 1.25:1, 2.5:1, 5:1, 10:1 and 20:1.

The amount of a composition according to the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

When applied to the useful plants component (A) is typically applied at a rate of 50 to 2000 g a.i./ha, particularly 100 to 1000 g a.i./ha and more particularly 300 to 500 g a.i./ha e.g. 300, 350, 400, 450 or 500 g a.i./ha, typically in association with 50 to 2000 g a.i./ha of component (B). The rate of application of component (B) depends on its identity. For example:

when component B is mesotrione, it is typically applied at a rate of 80-300 g a.i./ha, e.g. 80, 100, 150, 200, 250 or 300 g a.i./ha;

when component B is S-metolachlor, it is typically applied at a rate of 500-1800 g a.i./ha, e.g. 500, 600, 700, 800, 900, 1000, 1100, 1200, 1300, 1400, 1500, 1600 or 1800 g a.i./ha;

when component B is bicyclopyrone, it is typically applied at a rate of 50-250 g a.i./ha, e.g. 50, 100, 150, 200 or 250 g a.i./ha;
when component B is atrazine, it is typically applied at a rate of 840-2000 g a.i./ha, e.g. 840, 900, 1000, 1100, 1200, 1300, 1400, 1500, 1600, 1700, 1800, 1900 or 2000 g a.i./ha;
when component B is terbuthylazine, it is typically applied at a rate of 700-900 g a.i./ha, e.g. 700, 750, 800, 840, 850, 900 g a.i./ha;

In agricultural practice the application rates of the composition according to the invention depend on the type of effect desired, and typically range from 100 to 4000 g of total composition per hectare.

Preferably the mixing ratio of compound of formula (I) to safener is from 100:1 to 1:10, especially from 20:1 to 1:1.

The compounds of the invention can be applied before or after planting of the crops, before weeds emerge (pre-emergence application) or after weeds emerge (post-emergence application), and are particularly effective when applied pre-emergence to the weeds.

It is possible that the safener and the compositions of the invention are applied simultaneously. For example, the safener and the composition of the invention might be applied to the locus pre-emergence or might be applied to the crop post-emergence. It is also possible that the safener and the composition of the invention are applied sequentially. For example, the safener might be applied before sowing the seeds as a seed treatment and the composition of the invention might be applied to the locus pre-emergence or might be applied to the crop post-emergence.

The composition of the invention may show a synergistic effect. This occurs whenever the action of an active ingredient combination is greater than the sum of the actions of the individual components.

The action to be expected E for a given active ingredient combination obeys the so-called Colby Formula and can be calculated as follows (Colby, S. R., Calculating synergistic and antagonistic responses of herbicide combination, Weeds, Vol. 15, pages 20-22; 1967):
ppm=milligrams of active ingredient (a.i.) per liter
X=% action by first active ingredient using p ppm of the active ingredient
Y=% action by second active ingredient sing q ppm of the active ingredient.

According to Colby, the expected (additive) action of active ingredients A+B using p+q ppm of active ingredient is $$E = X + Y - \frac{X \cdot Y}{100}$$

If the action actually observed O is greater than the expected action E then the action of the combination is super-additive, i.e. there is a synergistic effect. In mathematical terms, synergism corresponds to a positive value for the difference of (O-E). In the case of purely complementary addition of activities (expected activity), said difference (O-E) is zero. A negative value of said difference (O-E) signals a loss of activity compared to the expected activity.

However, besides the actual synergistic action with respect to herbicidal activity, the composition according to the invention may also have further surprising advantageous properties. Examples of such advantageous properties that may be mentioned are: more advantageuos degradability; improved toxicological and/or ecotoxicological behaviour; or improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination.

Various aspects and embodiments of the present invention will now be illustrated in more detail by way of example. It will be appreciated that modification of detail may be made without departing from the scope of the invention.

For the avoidance of doubt, where a literary reference, patent application, or patent, is cited within the text of this application, the entire text of said citation is herein incorporated by reference.

EXAMPLES

Example 1—Herbicidal Action

Seeds of a variety of test species were sown in standard soil in pots. After cultivation for one day (pre-emergence) under controlled conditions in a glasshouse (at 24/18° C., at day/night; 16 hours light; 65% humidity), the plants were sprayed with an aqueous spray solution derived from the formulation of the technical active ingredient dissolved in acetone plus formulation A containing 10.56 wt % Emulsogen EL, 42.22 wt % N-MethylPyrrolidon, 2.22 wt % DPG-Monoethyl ether at a 1:20 ratio (technical active ingredient: formulation A). To achieve the mixture treatments, the appropriate concentration of the mixture partner (commercial formulation) was added to the solution in order to achieve the desired experimental compound:mixture partner ratio).

After application, the test plants were grown in a glasshouse under controlled conditions (at 24/18° C. day/night; 16 hours light; 65% humidity) and watered twice daily. Herbicidal activity was evaluated 21 days after application in a 100-0 scale (100=total damage to plant; 0=no damage to plant).

The results are shown in Table 2 to 7 below.

TABLE 2

Activity (% of untreated) against *Euphorbia heterophylla* (EPHHL)

| a/a | Bicyclopyrone (g/ha) | Compound:Mixing partner | Activity (% of untreated) Observed | Expected |
|---|---|---|---|---|
| | Compound 1.1 (g/ha) | | | |
| 1 | 0 | 10 | 32.5 | |
| 2 | 0 | 25 | 77.5 | |
| 3 | 100 | 0 | 12.5 | |

TABLE 2-continued

Activity (% of untreated) against *Euphorbia heterophylla* (EPHHL)

| a/a | Bicyclopyrone (g/ha) | | Compound:Mixing partner | Activity (% of untreated) | |
|---|---|---|---|---|---|
| | | | | Observed | Expected |
| 4 | 250 | 0 | | 70 | |
| 5 | 100 | 10 | 10:1 | 50 | 41 |
| 6 | 250 | 25 | 10:1 | 100 | 93 |
| Compound 1.2 (g/ha) | | | | | |
| 1 | 0 | 10 | | 32.5 | |
| 2 | 0 | 25 | | 77.5 | |
| 3 | 100 | 0 | | 10 | |
| 4 | 250 | 0 | | 80 | |
| 5 | 100 | 10 | 10:1 | 62.5 | 39 |
| 6 | 250 | 25 | 10:1 | 100 | 96 |
| Compound 1.3 (g/ha) | | | | | |
| 1 | 0 | 25 | | 95 | |
| 2 | 0 | 50 | | 98.5 | |
| 3 | 0 | 100 | | 100 | |
| 4 | 31.25 | 0 | | 5 | |
| 5 | 62.5 | 0 | | 15 | |
| 6 | 125 | 0 | | 35 | |
| 7 | 250 | 0 | | 87.5 | |
| 8 | 500 | 0 | | 100 | |
| 9 | 31.25 | 25 | 1.25:1 | 97.5 | 95 |
| 10 | 62.5 | 25 | 2.5:1 | 97.5 | 96 |
| 11 | 125 | 25 | 5:1 | 100 | 97 |
| 12 | 250 | 25 | 10:1 | 99.5 | 99 |
| 13 | 500 | 25 | 20:1 | 100 | 100 |

TABLE 3

Activity (% of untreated) against *Ipomea purpurea* (PHBPU)

| a/a | Compound 1.1 (g/ha) | Bicyclopyrone (g/ha) | Compound:Mixing partner | Activity (% of untreated) | |
|---|---|---|---|---|---|
| | | | | Observed | Expected |
| 1 | 0 | 10 | | 0 | |
| 2 | 0 | 25 | | 0 | |
| 3 | 100 | 0 | | 0 | |
| 4 | 250 | 0 | | 5 | |
| 5 | 100 | 10 | 10:1 | 0 | 0 |
| 6 | 250 | 25 | 10:1 | 60 | 5 |

| a/a | Compound 1.2 (g/ha) | Bicyclopyrone (g/ha) | Compound:Mixing partner | Observed | Expected |
|---|---|---|---|---|---|
| 1 | 0 | 10 | | 0 | |
| 2 | 0 | 25 | | 0 | |
| 3 | 100 | 0 | | 2.5 | |
| 4 | 250 | 0 | | 35 | |
| 5 | 100 | 10 | 10:1 | 0 | 3 |
| 6 | 250 | 25 | 10:1 | 55 | 35 |

| a/a | Compound 1.3 (g/ha) | Mesotrione (g/ha) | Compound:Mixing partner | Observed | Expected |
|---|---|---|---|---|---|
| 1 | 0 | 25 | | 0 | |
| 2 | 0 | 50 | | 0 | |
| 3 | 0 | 100 | | 50 | |
| 4 | 31.25 | 0 | | 67.5 | |
| 5 | 62.5 | 0 | | 97.5 | |
| 6 | 125 | 0 | | 40 | |
| 7 | 250 | 0 | | 85 | |
| 8 | 500 | 0 | | 100 | |
| 9 | 31.25 | 50 | 0.625:1 | 86.5 | 68 |
| 10 | 62.5 | 50 | 1.25:1 | 97.5 | 98 |
| 11 | 125 | 50 | 2.5:1 | 82.5 | 40 |
| 12 | 250 | 50 | 5:1 | 100 | 85 |
| 13 | 500 | 50 | 10:1 | 100 | 100 |

TABLE 3-continued

Activity (% of untreated) against *Ipomea purpurea* (PHBPU)

| a/a | Compound 1.3 (g/ha) | Bicyclopyrone (g/ha) | Compound:Mixing partner | Observed | Expected |
|---|---|---|---|---|---|
| 1 | 0 | 25 | | 0 | |
| 2 | 0 | 50 | | 0 | |
| 3 | 0 | 100 | | 50 | |
| 4 | 31.25 | 0 | | 67.5 | |
| 5 | 62.5 | 0 | | 97.5 | |
| 6 | 125 | 0 | | 50 | |
| 7 | 250 | 0 | | 72.5 | |
| 8 | 500 | 0 | | 90 | |
| 9 | 125 | 50 | 2.5:1 | 75 | 50 |
| 10 | 250 | 50 | 5:1 | 100 | 73 |
| 11 | 500 | 50 | 10:1 | 99 | 90 |
| 12 | 31.25 | 100 | 0.3125:1 | 87.5 | 84 |
| 13 | 62.5 | 100 | 0.625:1 | 100 | 99 |
| 14 | 125 | 100 | 1.25:1 | 100 | 75 |
| 15 | 250 | 100 | 2.5:1 | 100 | 86 |
| 16 | 500 | 100 | 5:1 | 100 | 95 |

TABLE 4

Activity (% of untreated) against *Ambrosia artimisifolia* (AMBEL)

| a/a | Compound 1.1 (g/ha) | Mesotrione (g/ha) | Compound:Mixing partner | Observed | Expected |
|---|---|---|---|---|---|
| 1 | 0 | 10 | | 7.5 | |
| 2 | 0 | 25 | | 50 | |
| 3 | 100 | 0 | | 37.5 | |
| 4 | 250 | 0 | | 85 | |
| 5 | 100 | 10 | 10:1 | 57.5 | 42 |
| 6 | 250 | 25 | 10:1 | 92 | 93 |

| a/a | Compound 1.1 (g/ha) | Bicyclopyrone (g/ha) | Compound:Mixing partner | Observed | Expected |
|---|---|---|---|---|---|
| 1 | 0 | 10 | | 70 | |
| 2 | 0 | 25 | | 90 | |
| 3 | 100 | 0 | | 37.5 | |
| 4 | 250 | 0 | | 85 | |
| 5 | 100 | 10 | 10:1 | 94 | 81 |
| 6 | 250 | 25 | 10:1 | 99 | 99 |

| a/a | Compound 1.2 (g/ha) | Mesotrione (g/ha) | Compound:Mixing partner | Observed | Expected |
|---|---|---|---|---|---|
| 1 | 0 | 10 | | 7.5 | |
| 2 | 0 | 25 | | 50 | |
| 3 | 100 | 0 | | 42.5 | |
| 4 | 250 | 0 | | 92.5 | |
| 5 | 100 | 10 | 10:1 | 72.5 | 47 |
| 6 | 250 | 25 | 10:1 | 99 | 96 |

| a/a | Compound 1.2 (g/ha) | Bicyclopyrone (g/ha) | Compound:Mixing partner | Observed | Expected |
|---|---|---|---|---|---|
| 1 | 0 | 10 | | 70 | |
| 2 | 0 | 25 | | 90 | |
| 3 | 100 | 0 | | 42.5 | |
| 4 | 250 | 0 | | 92.5 | |
| 5 | 100 | 10 | 10:1 | 94 | 83 |
| 6 | 250 | 25 | 10:1 | 99 | 99 |

| a/a | Compound 1.3 (g/ha) | Mesotrione (g/ha) | Compound:Mixing partner | Observed | Expected |
|---|---|---|---|---|---|
| 1 | 0 | 25 | | 0 | |
| 2 | 0 | 50 | | 12.5 | |
| 3 | 0 | 100 | | 25 | |
| 4 | 31.25 | 0 | | 85 | |
| 5 | 62.5 | 0 | | 97 | |
| 6 | 125 | 0 | | 85 | |

TABLE 4-continued

| Activity (% of untreated) against *Ambrosia artimisifolia* (AMBEL) | | | | |
|---|---|---|---|---|
| 7 | 250 | 0 | | 86 | |
| 8 | 500 | 0 | | 98.5 | |
| 9 | 31.25 | 100 | 0.3125:1 | 98.5 | 89 |
| 10 | 62.5 | 100 | 0.625:1 | 99.5 | 98 |
| 11 | 125 | 100 | 1.25:1 | 100 | 89 |
| 12 | 250 | 100 | 2.5:1 | 100 | 90 |
| 13 | 500 | 100 | 5:1 | 100 | 99 |

| a/a | Compound 1.3 (g/ha) | Bicyclopyrone (g/ha) | Compound:Mixing partner | Observed | Expected |
|---|---|---|---|---|---|
| 1 | 0 | 25 | | 0 | |
| 2 | 0 | 50 | | 12.5 | |
| 3 | 0 | 100 | | 25 | |
| 4 | 31.25 | 0 | | 85 | |
| 5 | 62.5 | 0 | | 97 | |
| 6 | 125 | 0 | | 98.5 | |
| 7 | 250 | 0 | | 99 | |
| 8 | 500 | 0 | | 99 | |
| 9 | 31.25 | 25 | 1.25:1 | 93.5 | 85 |
| 10 | 62.5 | 25 | 2.5:1 | 98 | 97 |
| 11 | 125 | 25 | 5:1 | 98 | 99 |
| 12 | 250 | 25 | 10:1 | 100 | 99 |
| 13 | 500 | 25 | 20:1 | 99.5 | 99 |

TABLE 5

Activity (% of untreated) against *Digitaria sanguinalis* (DIGSA)

| a/a | Compound 1.1 (g/ha) | Mesotrione (g/ha) | Compound:Mixing partner | Activity (% of untreated) Observed | Expected |
|---|---|---|---|---|---|
| 1 | 0 | 10 | | 45 | |
| 2 | 0 | 25 | | 96 | |
| 3 | 100 | 0 | | 0 | |
| 4 | 250 | 0 | | 65 | |
| 5 | 100 | 10 | 10:1 | 50 | 45 |
| 6 | 250 | 25 | 10:1 | 98.5 | 99 |

| a/a | Compound 1.1 (g/ha) | Bicyclopyrone (g/ha) | Compound:Mixing partner | Observed | Expected |
|---|---|---|---|---|---|
| 1 | 0 | 10 | | 87.5 | |
| 2 | 0 | 25 | | 98.5 | |
| 3 | 100 | 0 | | 0 | |
| 4 | 250 | 0 | | 65 | |
| 5 | 100 | 10 | 10:1 | 96.5 | 88 |
| 6 | 250 | 25 | 10:1 | 100 | 99 |

| a/a | Compound 1.1 (g/ha) | S-Metolachlor (g/ha) | Compound:Mixing partner | Observed | Expected |
|---|---|---|---|---|---|
| 1 | 0 | 80 | | 65 | |
| 2 | 0 | 200 | | 100 | |
| 3 | 100 | 0 | | 0 | |
| 4 | 250 | 0 | | 65 | |
| 5 | 100 | 80 | 1.25:1 | 75 | 65 |
| 6 | 250 | 200 | 1.25:1 | 99.5 | 100 |

| a/a | Compound 1.2 (g/ha) | Mesotrione (g/ha) | Compound:Mixing partner | Observed | Expected |
|---|---|---|---|---|---|
| 1 | 0 | 10 | | 45 | |
| 2 | 0 | 25 | | 96 | |
| 3 | 100 | 0 | | 0 | |
| 4 | 250 | 0 | | 5 | |
| 5 | 100 | 10 | 10:1 | 60 | 45 |
| 6 | 250 | 25 | 10:1 | 94.5 | 96 |

TABLE 5-continued

Activity (% of untreated) against *Digitaria sanguinalis* (DIGSA)

| a/a | Compound 1.2 (g/ha) | Bicyclopyrone (g/ha) | Compound:Mixing partner | Observed | Expected |
|---|---|---|---|---|---|
| 1 | 0 | 10 | | 87.5 | |
| 2 | 0 | 25 | | 98.5 | |
| 3 | 100 | 0 | | 0 | |
| 4 | 250 | 0 | | 5 | |
| 5 | 100 | 10 | 10:1 | 85 | 88 |
| 6 | 250 | 25 | 10:1 | 98.5 | 99 |

| a/a | Compound 1.2 (g/ha) | S-Metolachlor (g/ha) | Compound:Mixing partner | Observed | Expected |
|---|---|---|---|---|---|
| 1 | 0 | 80 | | 65 | |
| 2 | 0 | 200 | | 100 | |
| 3 | 100 | 0 | | 0 | |
| 4 | 250 | 0 | | 5 | |
| 5 | 100 | 80 | 1.25:1 | 85 | 65 |
| 6 | 250 | 200 | 1.25:1 | 100 | 100 |

| a/a | Compound 1.3 (g/ha) | Mesotrione (g/ha) | Compound:Mixing partner | Observed | Expected |
|---|---|---|---|---|---|
| 1 | 0 | 25 | | 0 | |
| 2 | 0 | 50 | | 5 | |
| 3 | 0 | 100 | | 0 | |
| 4 | 31.25 | 0 | | 0 | |
| 5 | 62.5 | 0 | | 65 | |
| 6 | 125 | 0 | | 99 | |
| 7 | 250 | 0 | | 100 | |
| 8 | 500 | 0 | | 99 | |
| 9 | 31.25 | 25 | 1.25:1 | 99.5 | 0 |
| 10 | 62.5 | 25 | 2.5:1 | 100 | 65 |
| 11 | 125 | 25 | 5:1 | 99.5 | 99 |
| 12 | 250 | 25 | 10:1 | 100 | 100 |
| 13 | 500 | 25 | 20:1 | 100 | 99 |
| 14 | 31.25 | 50 | 0.625:1 | 95 | 5 |
| 15 | 62.5 | 50 | 1.25:1 | 100 | 67 |
| 16 | 125 | 50 | 2.5:1 | 100 | 99 |
| 17 | 250 | 50 | 5:1 | 100 | 100 |
| 18 | 500 | 50 | 10:1 | 100 | 99 |
| 19 | 31.25 | 100 | 0.3125:1 | 100 | 0 |
| 20 | 62.5 | 100 | 0.625:1 | 100 | 65 |
| 21 | 125 | 100 | 1.25:1 | 100 | 99 |
| 22 | 250 | 100 | 2.5:1 | 100 | 100 |
| 23 | 500 | 100 | 5:1 | 100 | 99 |

| a/a | Compound 1.3 (g/ha) | Bicyclopyrone (g/ha) | Compound:Mixing partner | Observed | Expected |
|---|---|---|---|---|---|
| 1 | 0 | 25 | | 0 | |
| 2 | 0 | 50 | | 5 | |
| 3 | 0 | 100 | | 0 | |
| 4 | 31.25 | 0 | | 0 | |
| 5 | 62.5 | 0 | | 65 | |
| 6 | 125 | 0 | | 99 | |
| 7 | 250 | 0 | | 100 | |
| 8 | 500 | 0 | | 99.5 | |
| 9 | 31.25 | 25 | 1.25:1 | 100 | 0 |
| 10 | 62.5 | 25 | 2.5:1 | 100 | 65 |
| 11 | 125 | 25 | 5:1 | 99.5 | 99 |
| 12 | 250 | 25 | 10:1 | 100 | 100 |
| 13 | 500 | 25 | 20:1 | 100 | 100 |
| 14 | 31.25 | 50 | 0.625:1 | 100 | 5 |
| 15 | 62.5 | 50 | 1.25:1 | 100 | 67 |
| 16 | 125 | 50 | 2.5:1 | 100 | 99 |
| 17 | 250 | 50 | 5:1 | 100 | 100 |
| 18 | 500 | 50 | 10:1 | 100 | 100 |
| 19 | 31.25 | 100 | 0.3125:1 | 100 | 0 |
| 20 | 62.5 | 100 | 0.625:1 | 100 | 65 |
| 21 | 125 | 100 | 1.25:1 | 100 | 99 |
| 22 | 250 | 100 | 2.5:1 | 100 | 100 |
| 23 | 500 | 100 | 5:1 | 100 | 100 |

TABLE 6

Activity (% of untreated against *Setaria fabarii* (SETFA))

| a/a | Compound 1.1 (g/ha) | Mesotrione (g/ha) | Compound:Mixing partner | Activity (% of untreated) Observed | Expected |
|---|---|---|---|---|---|
| 1 | 0 | 10 | | 0 | |
| 2 | 0 | 25 | | 0 | |
| 3 | 100 | 0 | | 0 | |
| 4 | 250 | 0 | | 70 | |
| 5 | 100 | 10 | 10:1 | 0 | 0 |
| 6 | 250 | 25 | 10:1 | 65 | 70 |

| a/a | Compound 1.1 (g/ha) | Bicyclopyrone (g/ha) | Compound:Mixing partner | Observed | Expected |
|---|---|---|---|---|---|
| 1 | 0 | 10 | | 17.5 | |
| 2 | 0 | 25 | | 77.5 | |
| 3 | 100 | 0 | | 0 | |
| 4 | 250 | 0 | | 70 | |
| 5 | 100 | 10 | 10:1 | 65 | 18 |
| 6 | 250 | 25 | 10:1 | 100 | 93 |

| a/a | Compound 1.1 (g/ha) | S-Metolachlor (g/ha) | Compound:Mixing partner | Observed | Expected |
|---|---|---|---|---|---|
| 1 | 0 | 80 | | 85 | |
| 2 | 0 | 200 | | 98.5 | |
| 3 | 100 | 0 | | 0 | |
| 4 | 250 | 0 | | 70 | |
| 5 | 100 | 80 | 1.25:1 | 92.5 | 85 |
| 6 | 250 | 200 | 1.25:1 | 100 | 100 |

| a/a | Compound 1.2 (g/ha) | Mesotrione (g/ha) | Compound:Mixing partner | Observed | Expected |
|---|---|---|---|---|---|
| 1 | 0 | 10 | | 0 | |
| 2 | 0 | 25 | | 0 | |
| 3 | 100 | 0 | | 0 | |
| 4 | 250 | 0 | | 72.5 | |
| 5 | 100 | 10 | 10:1 | 5 | 0 |
| 6 | 250 | 25 | 10:1 | 81.5 | 73 |

| a/a | Compound 1.2 (g/ha) | Bicyclopyrone (g/ha) | Compound:Mixing partner | Observed | Expected |
|---|---|---|---|---|---|
| 1 | 0 | 10 | | 17.5 | |
| 2 | 0 | 25 | | 77.5 | |
| 3 | 100 | 0 | | 0 | |
| 4 | 250 | 0 | | 72.5 | |
| 5 | 100 | 10 | 10:1 | 70 | 18 |
| 6 | 250 | 25 | 10:1 | 99.5 | 94 |

| a/a | Compound 1.2 (g/ha) | S-Metolachlor (g/ha) | Compound:Mixing partner | Observed | Expected |
|---|---|---|---|---|---|
| 1 | 0 | 80 | | 85 | |
| 2 | 0 | 200 | | 98.5 | |
| 3 | 100 | 0 | | 0 | |
| 4 | 250 | 0 | | 72.5 | |
| 5 | 100 | 80 | 1.25:1 | 90 | 85 |
| 6 | 250 | 200 | 1.25:1 | 100 | 100 |

| a/a | Compound 1.3 (g/ha) | Mesotrione (g/ha) | Compound:Mixing partner | Observed | Expected |
|---|---|---|---|---|---|
| 1 | 0 | 25 | | 15 | |
| 2 | 0 | 50 | | 35 | |
| 3 | 0 | 100 | | 57.5 | |
| 4 | 31.25 | 0 | | 90 | |
| 5 | 62.5 | 0 | | 100 | |
| 6 | 125 | 0 | | 0 | |
| 7 | 250 | 0 | | 20 | |

TABLE 6-continued

| Activity (% of untreated against *Setaria fabarii* (SETFA) | | | | |
|---|---|---|---|---|
| 8 | 500 | 0 | | 40 |
| 9 | 125 | 25 | 5:1 | 60 | 15 |
| 10 | 250 | 25 | 10:1 | 92.5 | 32 |
| 11 | 500 | 25 | 20:1 | 96 | 49 |
| 12 | 125 | 50 | 2.5:1 | 60 | 35 |
| 13 | 250 | 50 | 5:1 | 90 | 48 |
| 14 | 500 | 50 | 10:1 | 100 | 61 |
| 15 | 125 | 100 | 1.25:1 | 67.5 | 58 |
| 16 | 250 | 100 | 2.5:1 | 100 | 66 |
| 17 | 500 | 100 | 5:1 | 100 | 75 |

| a/a | Compound 1.3 (g/ha) | Bicyclopyrone (g/ha) | Compound:Mixing partner | Observed | Expected |
|---|---|---|---|---|---|
| 1 | 0 | 25 | | 15 | |
| 2 | 0 | 50 | | 35 | |
| 3 | 0 | 100 | | 57.5 | |
| 4 | 31.25 | 0 | | 90 | |
| 5 | 62.5 | 0 | | 100 | |
| 6 | 125 | 0 | | 67.5 | |
| 7 | 250 | 0 | | 96.5 | |
| 8 | 500 | 0 | | 98 | |
| 9 | 31.25 | 50 | 0.625:1 | 99 | 94 |
| 10 | 62.5 | 50 | 1.25:1 | 98.5 | 100 |
| 11 | 125 | 50 | 2.5:1 | 99.5 | 79 |
| 12 | 250 | 50 | 5:1 | 100 | 98 |
| 13 | 500 | 50 | 10:1 | 100 | 99 |
| 14 | 31.25 | 100 | 0.3125:1 | 100 | 96 |
| 15 | 62.5 | 100 | 0.625:1 | 100 | 100 |
| 16 | 125 | 100 | 1.25:1 | 100 | 86 |
| 17 | 250 | 100 | 2.5:1 | 100 | 99 |
| 18 | 500 | 100 | 5:1 | 100 | 99 |

TABLE 7

| Activity (% of untreated) against *Bidens pilosa* (BIDPI) | | | | |
|---|---|---|---|---|
| a/a | Compound 1.2 (g/ha) | Compound:Mixing partner | Activity (% of untreated) | |
| | | | Observed | Expected |
| | | Mesotrione (g/ha) | | |
| 1 | 0 | 10 | | 10 | |
| 2 | 0 | 25 | | 30 | |
| 3 | 100 | 0 | | 65 | |
| 4 | 250 | 0 | | 85 | |
| 5 | 100 | 10 | 10:1 | 70 | 69 |
| 6 | 250 | 25 | 10:1 | 99.5 | 90 |
| | | Bicyclopyrone | | |
| 1 | 0 | 10 | | 0 | |
| 2 | 0 | 25 | | 5 | |
| 3 | 100 | 0 | | 65 | |
| 4 | 250 | 0 | | 85 | |
| 5 | 100 | 10 | 10:1 | 87.5 | 65 |
| 6 | 250 | 25 | 10:1 | 99.5 | 86 |

The invention claimed is:
1. A composition comprising:
(A) 1.1
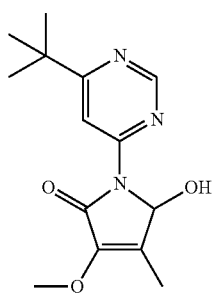
and (B) bicyclopyrone;
(A) 1.1
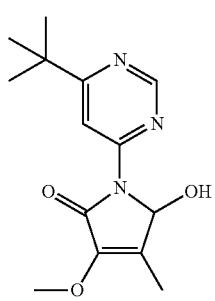
and (B) mesotrione;
(A) 1.1
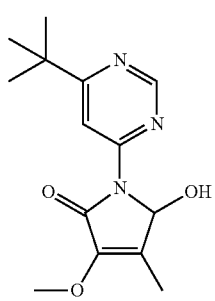
and (B) S-metolachlor;
(A) 1.2
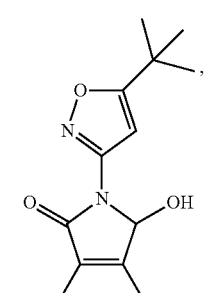
and (B) bicyclopyrone;
(A) 1.2
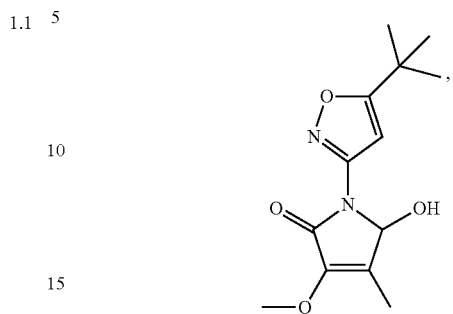
and (B) mesotrione;
(A) 1.2
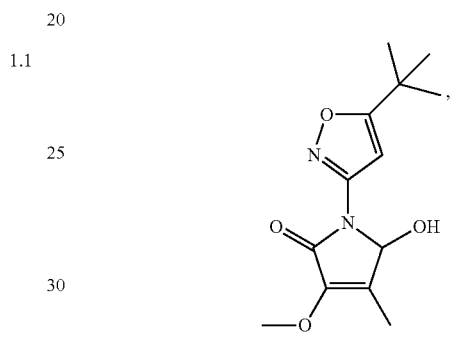
and (B) S-metolachlor;
(A) 1.3
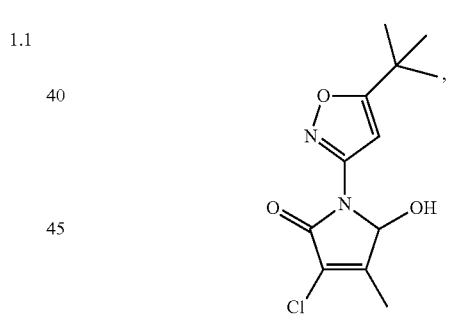
and (B) bicyclopyrone; or
(A) 1.3
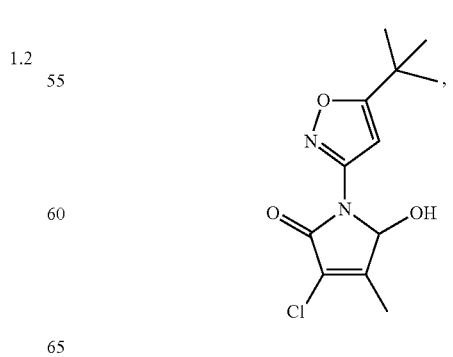
and (B) mesotrione;
wherein the ratio of (A) to (B) is 10:1 to 0.3125:1.

2. The composition of claim 1, wherein the composition is (A) 1.1

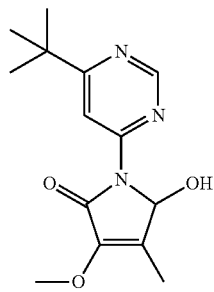 [SMILES: COC1=C(C)C(O)N(c2cc(C(C)(C)C)ncn2)C1=O]

1.1 and (B) bicyclopyrone.

3. The composition of claim 1, wherein the composition is (A) 1.1

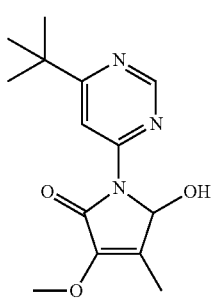

1.1 and (B) mesotrione.

4. The composition of claim 1, wherein the composition is (A) 1.1

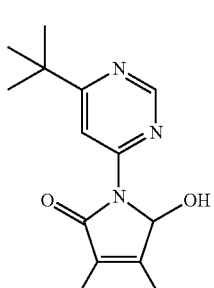

1.1 and (B) S-metolachlor.

5. The composition of claim 1, wherein the composition is (A) 1.2

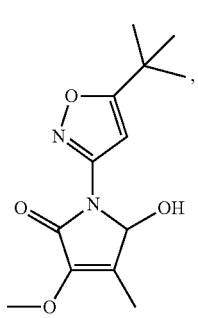

1.2 and (B) bicyclopyrone.

6. The composition of claim 1, wherein the composition is (A) 1.2

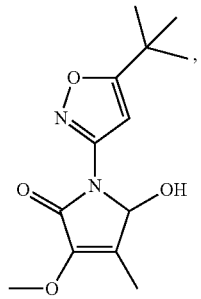

1.2 and (B) mesotrione.

7. The composition of claim 1, wherein the composition is (A) 1.2

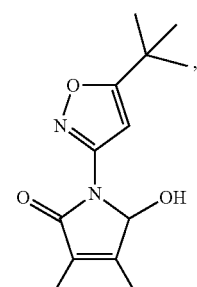

1.2 and (B) S-metolachlor.

8. The composition of claim 1, wherein the composition is (A) 1.3

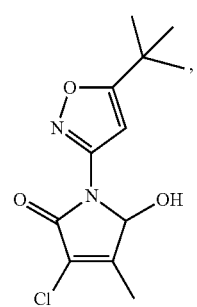

1.3 and (B) bicyclopyrone.

9. The composition of claim 1, wherein the composition is (A) 1.3

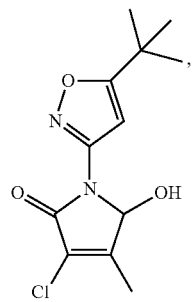

and (B) mesotrione.

10. The composition of claim 1, which further includes one or more safeners selected from the group consisting of AD 67, benoxacor, cloquintocet-mexyl, cyometrinil, cyprosulfamide, dichlormid, dicyclonon, dietholate, fenchlorazole-ethyl, fenclorim, flurazole, fluxofenim, furilazole, furilazome, isoxadifen-ethyl, mefenpyr-diethyl, mephenate, oxabetrinil, naphthalic anhydride, TI-35, N-isopropyl-4-(2-methoxy-benzoylsulfamoyl)-benzamide and N-(2-methoxy-benzoyl)-4-[(methylaminocarbonyl)amino]benzenesulfonamide.

11. A method of controlling plants, comprising applying to the plants or to the locus of the plants, a herbicidally effective amount of a composition as defined in claim 1.

12. A method of controlling weeds in crops of useful plants, comprising applying to the weeds or to the locus of the weeds, or to the useful plants or to the locus of the useful plants, a herbicidally effective amount of a composition as defined in claim 1.

13. The method of claim 12, wherein component (A) is applied at a rate of 300 to 500 g a.i/ha.

* * * * *